(12) United States Patent
Birkinshaw et al.

(10) Patent No.: US 7,754,735 B2
(45) Date of Patent: Jul. 13, 2010

(54) SUBSTITUTED INDOLES

(75) Inventors: Timothy Birkinshaw, Leicestershire (GB); Roger Bonnert, Leicestershire (GB); Tony Cook, Leicestershire (GB); Rukhsana Rasul, Leicestershire (GB); Hitesh Sanganee, Leicestershire (GB); Simon Teague, Leicestershire (GB)

(73) Assignee: AstraZeneca AB, Sodertalje (SE)

( * ) Notice: Subject to any disclaimer, the term of this patent is extended or adjusted under 35 U.S.C. 154(b) by 1114 days.

(21) Appl. No.: 10/516,165

(22) PCT Filed: May 27, 2003

(86) PCT No.: PCT/SE03/00855

§ 371 (c)(1),
(2), (4) Date: Nov. 30, 2004

(87) PCT Pub. No.: WO03/101981

PCT Pub. Date: Dec. 11, 2003

(65) Prior Publication Data

US 2005/0222201 A1 Oct. 6, 2005

(30) Foreign Application Priority Data

May 30, 2002 (SE) .................................. 0201636
Dec. 20, 2002 (SE) .................................. 0203822

(51) Int. Cl.
*A61K 31/4709* (2006.01)
*A61K 31/405* (2006.01)
*C07D 401/04* (2006.01)

(52) U.S. Cl. ........................ 514/314; 514/414; 546/167; 548/464

(58) Field of Classification Search .................. 514/314, 514/414; 546/167; 548/464
See application file for complete search history.

(56) References Cited

U.S. PATENT DOCUMENTS

| 5,459,150 | A | 10/1995 | Brooks et al. |
| 5,486,525 | A | 1/1996 | Summers, Jr. et al. |
| 5,567,711 | A | 10/1996 | Sheppard et al. |
| 6,916,841 | B2 | 7/2005 | Seehra et al. |
| 6,933,316 | B2 | 8/2005 | Hsieh et al. |
| 7,166,607 | B2 | 1/2007 | Bonnert et al. |
| 2005/0222201 | A1 | 10/2005 | Birkinshaw et al. |
| 2006/0111426 | A1 | 5/2006 | Bonnert et al. |
| 2006/0264444 | A1 | 11/2006 | Bonnert et al. |
| 2008/0027092 | A1 | 1/2008 | Bonnert et al. |
| 2008/0051586 | A1 | 2/2008 | Keegan et al. |
| 2008/0249110 | A1 | 10/2008 | Bonnert et al. |
| 2009/0143449 | A1 | 6/2009 | Bonnert et al. |

FOREIGN PATENT DOCUMENTS

| EP | 0254241 | 1/1988 |
| EP | 0530907 A1 | 3/1993 |
| EP | 0576347 A1 | 12/1993 |
| EP | 0 924 209 B1 | 6/1999 |
| EP | 1 170 594 A2 | 1/2002 |
| EP | 1505061 | 2/2005 |
| GB | 1356834 | 6/1974 |
| GB | 2422831 | 8/2006 |
| WO | WO94/19321 | 9/1994 |
| WO | WO95/16687 | 6/1995 |
| WO | WO 98/13368 | 4/1998 |
| WO | WO 99/09007 | 2/1999 |
| WO | WO 00/78761 A1 | 12/2000 |
| WO | WO 01/032621 | 5/2001 |
| WO | WO 01/47922 A2 | 7/2001 |
| WO | WO 0147922 A2 * | 7/2001 |
| WO | WO01/92224 A1 | 12/2001 |
| WO | WO03/064387 A2 | 8/2003 |
| WO | WO 03/066046 | 8/2003 |
| WO | WO 03/066047 | 8/2003 |
| WO | WO03/097598 | 11/2003 |
| WO | WO 03/101961 | 12/2003 |
| WO | WO 03/101981 | 12/2003 |
| WO | WO 2004/007451 | 1/2004 |
| WO | WO 2004/016609 A1 | 2/2004 |
| WO | WO 2004/106302 | 12/2004 |
| WO | WO 2005/019171 | 3/2005 |
| WO | WO 2005/040114 | 5/2005 |
| WO | WO 2005/054232 | 6/2005 |
| WO | WO 2006/075139 | 7/2006 |
| WO | WO 2007/138282 | 12/2007 |
| WO | WO 2007/140786 | 12/2007 |
| WO | WO 2008/000409 | 1/2008 |

OTHER PUBLICATIONS

Atkinson et al., "A New Synthesis of 3-Arylthioindoles", *Synthesis* 6:480-481 (1988).
Cecil Textbook of Medicine, 20th edition, vol. 2:1992-1996 (1996).
Cecil Textbook of Medicine, 20th edition, vol. 2:2050-2057 (1996).
FDA mulls drug to slow late-stage Alzheimer's [online], [retrieved on Sep. 23, 2003]. Retrieved from the Internet, URL:http://www.cnn.com/2003/HEALTH/conditions/09/24/alzheimers.drug.ap/indexhtml>.

(Continued)

*Primary Examiner*—Joseph R Kosack
(74) *Attorney, Agent, or Firm*—Fish & Richardson P.C.

(57) ABSTRACT

The present invention relates to substituted indoles of formula (I), useful as pharmaceutical compounds for treating respiratory disorders.

12 Claims, No Drawings

OTHER PUBLICATIONS

Database CA 'Online! Chemical Abstracts Service, Columbus, Ohio, US; Tanimoto, Norihiko et al: "Preparation of indole derivatives as PGD2 receptor antagonists" XP002301963 retrieved from STN Database accession No. 2003:931327.

Garcia et al., "A Novel Synthesis of 3-Cyanoindoles and a New Route to Indole-3-Carboxylic Acid Derivatives", *Tetrahedron Letters* 26(15):1827-1830 (1985).

Hamel et al., "Regioselective Synthesis of Mixed Indole 2,3-Bis-(sulfides). A Study of the Mechanism of the Second Sulfenylation of Indole", *J. Org. Chem.* 61:1573-1577 (1996).

Howard et al., "Synthesis and aldose reductase inhibitory activity of substituted 2(1*H*)-benzimidazolone- and oxindole-1-acetic acids", *Eur J Med Chem* 27:779-789 (1992).

Lüscher et al., "Deblocking of *o*-Nitrophenylsulfenyl-Protected Peptides by Ammonium Thiocyanate and (2-Methyl-1-indolyl)acetic acid", *Helv. Chim. Acta* 66(2):602-605 (1983).

Matassa et al., "Evolution of a Series of Peptidoleukotriene Antagonists: Synthesis and Structure/Activity Relationships of 1,3,5-Substituted Indoles and Indazoles", *J. Med. Chem.* 33:1781-1790 (1990).

Matsugi et al., "An efficient sylfenylation of aromatics using highly active quinone mono *O,S*-acetal bearing a pentafluorophenylthio group", *Tetrahedron Letters* 42:1077-1080 (2001).

Matsugi et al., "Facile and Efficient Sulfenylation Method Using Quinone Mono-*O,S*-Acetals under Mild Conditions", *J. Org. Chem.* 66:2434-2441 (2001).

Ovenden et al., "Echinosulfonic Acids A-C and Echinosulfone A: Novel Bromoindole Sulfonic Acids and a Sulfone from a Southern Australian Marine Sponge, *Echinodictyum*", *J. Nat. Prod.* 62:1246-1249 (1999).

STN International, CAPLUS accession No. 1977:535057, Document No. 87:135057, Sankyo Co., Ltd., "3-Indolyl thio ethers", & JP,A2,52039671, 19770328, RN 64137-76-4, 54491-43-9, 56366-45-1.

STN International, CAPLUS accession No. 2001:338492, Document No. 134:353315, Wakunaga Pharmaceutical Co., Ltd., "Preparation of indole derivatives as chymase inhibitors and drugs containing the same as the active ingredient", & WO,A1,2001032621, 20010510, RN 64137-76-4, 336186-33-5.

STN International, CHEMCATS accession No. 2000:1027702, Apr. 26, 2001, 8004-3013, "1H-Indole-1-acetic acid, 2-methyl-3-(phenylthio)-, ethyl ester", CAS Registry No. 300860-50-8.

STN International, file CAPLUS, CAPUS accession No. 1995:401159, Document No. 122:187576, Yoshitomi Pharmaceutical Industries, Ltd., "Preparation of fused pyrazole derivatives", & JP,A2,06206872, 19940726.

Hary et al., "Efficient synthesis of 3-(4,5-dihydro-1*H*-imidazole-2-yl)-1*H*-indoles", *Tetrahedron Letters* 42:5187-5189 (2001).

STN International, CAPLUS accession No. 2001:235566, Document No. 134:266203, Kato, Susumu et al.: "Preparation and application of benzopyranone derivatives"; & JP,A2,2001089471, 20010403, RN 332082-10-7.

STN International, CAPLUS accession No. 1980:6356, Document No. 92:6356, Gabrielyan, G.E. et al.: "Indole derivatives. LX. Synthesis of indole compounds with a furan ring", & Armyanskii Khimicheskii Zhurnal (1979), 32(4), 309-14, RN 51842-57-0.

Morissette et al., "High-throughput crystallization: polymorphs, salts, co-crystals and solvates of pharmaceutical solids", *Advanced Drug Delivery Reviews* 56:275-300 (2004).

Patani and LaVoie, "Bioisosterism: A Rational Approach in Drug Design", *Chem Rev.* 96:3147-3176 (1996).

Vippagunta et al., abstract, "Crystalline solids", *Advanced Drug Delivery Reviews* 48:3-26 (2001).

"COPD: Causes and Prevention." NIH SeniorHealth. National Heart, Lung, and Blood Institute. Accessed Apr. 6, 2009. <http://nihseniorhealth.gov/copd/causesandprevention/01.html>.

"Prevention of Cystic Fibrosis." WrongDiagnosis.com. Accessed Apr. 6, 2009. <http://www.wrongdiagnosis.com/c/cf/prevent.htm>.

\* cited by examiner

SUBSTITUTED INDOLES

CROSS-REFERENCE TO RELATED APPLICATIONS

This application is the national phase application under 35 U.S.C. § 371 of PCT International Application No. PCT/SE03/00855, filed May 27, 2003, which claims priority to Swedish Application Serial No. 0201636-8, filed May 30, 2002 and Swedish Application Serial No. 0203822-2, filed Dec. 20, 2002.

The present invention relates to substituted indoles useful as pharmaceutical compounds for treating respiratory disorders, pharmaceutical compositions containing them, and processes for their preparation.

EPA 1 170 594 discloses methods for the identification of compounds useful for the treatment of disease states mediated by prostaglandin D2, a ligand for orphan receptor CRTh2. GB 1356834 discloses a series of compounds said to possess anti-inflammatory, analgesic and antipyretic activity. It has now surprisingly been found that certain indole acetic acids are active at the CRTh2 receptor, and as a consequence are expected to be potentially useful for the treatment of various respiratory diseases, including asthma and COPD.

In a first aspect the invention therefore provides a compound of formula (I) or a pharmaceutically acceptable salt or solvate thereof:

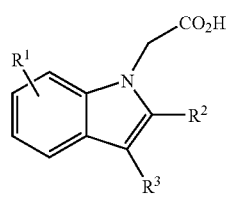

in which in which $R^1$ is hydrogen, halogen, CN, nitro, $SO_2R^4$, OH, $OR^4$, $SR^4$, $SOR^4$, $SO_2NR^5R^6$, $CONR^5R^6$, $NR^5R^6$, $NR^9SO_2R^4$, $NR^9CO_2R^4$, $NR^9COR^4$, heteroaryl, aryl (optionally substituted by chlorine or fluorine), $C_2$-$C_6$ alkenyl, $C_2$-$C_6$ alkynyl or $C_{1-6}$alkyl, the latter three groups being optionally substituted by one or more substituents independently selected from halogen, $OR^8$ and $NR^5R^6$, $S(O)_xR^7$ where x is 0, 1 or 2;

$R^2$ is hydrogen, halogen, CN, $SO_2R^4$ or $CONR^5R^6$, $CH_2OH$, $CH_2OR^4$ or $C_{1-7}$alkyl, the latter group being optionally substituted by one or more substituents independently selected from halogen atoms, $OR^8$ and $NR^5R^6$, $S(O)_xR^7$ where x is 0, 1 or 2;

$R^3$ is quinoline, 1,2-benzisothiazole, benzo[b]thiophene or indole each of which is optionally substituted by one or more substituents independently selected from hydrogen, halogen, CN, nitro, OH, $SO_2R^4$, $OR^4$, $SR^4$, $SOR^4$, $SO_2NR^5R^6$, $CONR^5R^6$, $NR^5R^6$, $NR^9SO_2R^4$, $NR^9CO_2R^4$, $NR^9CO_2H$, $NR^9COR^4$, $C_2$-$C_6$ alkenyl, $C_2$-$C_6$ alkynyl, $C_{1-6}$ alkyl, the latter three groups being optionally substituted by one or more substituents independently selected from halogen atoms, $OR^8$ and $NR^5R^6$, $S(O)_xR^7$ where x=0, 1 or 2;

$R^4$ represents aryl, heteroaryl, or $C_{1-6}$alkyl all of which may be optionally substituted by one or more substituents independently selected from halogen atoms, aryl, heteroaryl, $OR^{10}$ and $NR^{11}R^{12}$, $S(O)_xR^{13}$ (where x=0, 1 or 2), $CONR^{14}R^{15}$, $NR^{14}COR^{15}$, $SO_2NR^{14}R^{15}$, $NR^{14}SO_2R^{15}$;

$R^5$ and $R^6$ independently represent a hydrogen atom, a $C_{1-6}$alkyl group, or an aryl, or a heteroaryl, the latter three of which may be optionally substituted by one or more substituents independently selected from halogen atoms, aryl, $OR^8$ and $NR^{14}R^{15}$, $CONR^{14}R^{15}$, $NR^{14}COR^{15}$, $SO_2NR^{14}R^{15}$, $NR^{14}SO_2R^{15}$;

or $R^5$ and $R^6$ together with the nitrogen atom to which they are attached can form a 3-8 membered saturated heterocylic ring optionally containing one or more atoms selected from O, $S(O)_x$ where x=0, 1 or 2, $NR^{16}$, and itself optionally substituted by $C_{1-3}$ alkyl;

$R^7$ and $R^{13}$ independently represent a $C_1$-$C_6$, alkyl, an aryl or a heteroaryl group all of which maybe optionally substituted by one or more halogen atoms;

$R^8$ represents a hydrogen atom, $C(O)R^9$, $C_1$-$C_6$ alkyl an aryl or a heteroaryl group, all of which may be optionally substituted by halogen atoms or an aryl group;

each of $R^9$ $R^{10}$, $R^{11}$, $R^{12}$, $R^{14}$, $R^{15}$, independently represents a hydrogen atom, $C_1$-$C_6$ alkyl, an aryl or a heteroaryl group, all of which may be optionally substituted by a halogen atom; and $R^{16}$ is hydrogen, $C_{1-4}$ alkyl, —$COC_1$-$C_4$ alkyl, $COYC_1$-$C_4$alkyl where Y is O or $NR^7$.

In the context of the present specification, unless otherwise indicated, an alkyl or alkenyl group or an alkyl or alkenyl moiety in a substituent group may be linear branched, or cyclic.

An example of aryl is phenyl or naphthyl.

Heteroaryl is defined as a 5-7 membered aromatic ring or can be 6,6- or 6,5-fused bicyclic each ring containing one or more heteroatoms selected from N, S and O. Examples include pyridine, pyrimidine, thiazole, oxazole, pyrazole, imidazole, furan, isoxazole, pyrrole, isothiazole and azulene, indene, quinoline, isoquinoline, indole, indolizine, benzo[b]furan, benzo[b]thiophene, 1H-indazole, benzimidazole, benzthiazole, benzisothiazole, benzisooxazole, benzoxazole, purine, 4H-quinolizine, cinnoline, phthalazine, quinazoline, quinoxaline, 1,8-naphthyridine, pteridine, quinolone.

Heterocyclic rings as defined for $R^5$ and $R^6$ means saturated heterocycles, examples include morpholine, thiomorpholine, azetidine, imidazolidine, pyrrolidine, piperidine and piperazine.

Preferably $R^1$ is hydrogen or $C_{1-6}$alkyl optionally substituted by halogen, $C_{1-6}$alkoxy, alkylsulfone, cyano, $NR^9SO_2R^4$, $NR^9COR^4$. More preferably $R^1$ is hydrogen, methyl, methoxy, chloro, fluoro, cyano, alkylsulfone, trifluoromethyl, $NHSO_2Me$, NHCOMe. The $R^1$ group(s) can be present at any suitable position on the indole ring, preferably the $R^1$ group(s) is (are) at the 4 and/or 5-position.

When $R^1$ is other than hydrogen, 1 to 4 substituents can be present. Preferably the number of substituents when $R^1$ is other than hydrogen is 1-2.

Preferably $R^2$ is hydrogen, $C_{1-6}$alkyl or $C_{1-6}$alkyl optionally substituted by $OR^8$, more preferably $R^2$ is methyl.

Suitably $R^3$ is quinoline, 1,2-benzisothiazole, benzo[b]thiophene or indole each of which is optionally substituted by one or more substituents independently selected from hydrogen, halogen, CN, nitro, OH, $SO_2R^4$, $OR^4$, $SR^4$, $SOR^4$, $SO_2NR^5R^6$, $CONR^5R^6$, $NR^5R^6$, $NR^9SO_2R^4$, $NR^9CO_2R^4$, $NR^9CO_2H$, $NR^9COR^4$, $C_2$-$C_6$ alkenyl, $C_2$-$C_6$ alkynyl, $C_{1-6}$ alkyl, the latter three groups being optionally substituted by one or more substituents independently selected from halogen atoms, $OR^8$ and $NR^5R^6$, $S(O)_xR^7$ where x=0, 1 or 2.

Preferably R³ is quinoline is attached to the indole at the 4 position, or 1,2-benzisothiazole and benziso[b]thiophene at the 3 positions. Most preferably R³ is quinoline is attached to the indole at the 4-position.

Substituents can be present on any suitable position of an R³ group. Preferred substituents include one or more selected from $C_{1-6}$ alkyl (optionally substituted by one or more substituents independently selected from halogen atoms, OR⁸ and NR⁵R⁶, $S(O)_xR^7$ where x is 0, 1 or 2), halogen, alkoxy, alkylsulfone, cyano, substituted alkyl. More preferably the substituents are hydrogen, methyl, trifluoromethyl, methoxy, fluoro, chloro, methylsulfone, cyano.

Where R³ is heteroaromatic, heteroatoms may be present at any suitable position of the R³ group.

If R³ is quinoline, preferably the substituents are present at the 2, 6,7 or (and) 8 positions. Preferably, the number of substituents other than hydrogen is 1-2.

Preferred compounds of the invention include:
3-(2-chloro-4-quinolinyl)-2,5-dimethyl-H-indole-1-acetic acid;
3-(2-chloro-4-quinolinyl)-2-methyl-1H-indole-1-acetic acid;
3-(2-chloro-4-quinolinyl)-1H-indole-1-acetic acid;
2-methyl-3-(4-quinolinyl)-1H-indole-1-acetic acid;
3-(2-chloro-4-quinolinyl)-5-methoxy-2-methyl-1H-indole-1-acetic acid;
3-(2-chloro-4-quinolinyl)-2,6-dimethyl-1H-indole-1-acetic acid;
3-(2-chloro-4-quinolinyl)-2,4-dimethyl-1H-indole-1-acetic acid;
3-(2-benzothiazolyl)-2,5-dimethyl-1H-indole-1-acetic acid;
2,5-dimethyl-3-(7-methyl-4-quinolinyl)-1H-indole-1-acetic acid;
2,5-dimethyl-3-(8-methyl-4-quinolinyl)-1H-indole-1-acetic acid;
3-(6-fluoro-4-quinolinyl)-2,5-dimethyl-1H-indole-1-acetic acid;
3-(1-isoquinolinyl)-2,5-dimethyl-1H-indole-1-acetic acid;
3-(6-methoxy-4-quinolinyl)-2,5-dimethyl-1H-indole-1-acetic acid;
2,5-dimethyl-3-(4-quinolinyl)-1H-indole-1-acetic acid;
2,5-dimethyl-3-[8-(trifluoromethyl)-4-quinolinyl]-1H-indole-1-acetic acid;
3-(2-benzoxazolyl)-2,5-dimethyl-1H-indole-1-acetic acid;
3-(1,2-benzisothiazol-3-yl)-2,5-dimethyl-1H-indole-1-acetic acid;
3-(7-chloro-4-quinolinyl)-2,5-dimethyl-6-(methylsulfonyl)-1H-indole-1-acetic acid;
3-(8-fluoro-4-quinolinyl)-2,5-dimethyl-1H-indole-1-acetic acid;
3-(2,8-dimethyl-4-quinolinyl)-2,5-dimethyl-1H-indole-1-acetic acid;
2,5-dimethyl-3-[7-(trifluoromethyl)-4-quinolinyl]-1H-indole-1-acetic acid;
3-(8-bromo-2-methyl-4-quinolinyl)-2,5-dimethyl-1H-indole-1-acetic acid;
3-(8-methoxy-2-methyl-4-quinolinyl)-2,5-dimethyl-1H-indole-1-acetic acid;
3-(6,8-dimethyl-4-quinolinyl)-2,5-dimethyl-1H-indole-1-acetic acid;
3-(8-chloro-4-quinolinyl)-2,5-dimethyl-1H-indole-1-acetic acid;
3-(7-chloro-4-quinolinyl)-2-methyl-5-nitro-1H-indole-1-acetic acid;
5-chloro-3-(7-chloro-4-quinolinyl)-2-methyl-1H-indole-1-acetic acid;
5-chloro-2-methyl-3-(8-methyl-4-quinolinyl)-1H-indole-1-acetic acid;
5-chloro-3-(6-methoxy-2-methyl-4-quinolinyl)-2-methyl-1H-indole-1-acetic acid;
5-methoxy-2-methyl-3-(8-methyl-4-quinolinyl)-1H-indole-1-acetic acid;
3-(7-chloro-4-quinolinyl)-5-fluoro-2-methyl-1H-indole-1-acetic acid;
5-fluoro-2-methyl-3-[8-(trifluoromethyl)-4-quinolinyl]-1H-indole-1-acetic acid;
5-fluoro-2-methyl-3-(8-methyl-4-quinolinyl)-1H-indole-1-acetic acid;
2-methyl-3-(8-methyl-4-quinolinyl)-5-(trifluoromethyl)-1H-indole-1-acetic acid;
3-(1,2-benzisothiazol-3-yl)-2-methyl-5-(trifluoromethyl)-1H-indole-1-acetic acid;
3-(1,2-benzisothiazol-3-yl)-5-fluoro-2-methyl-1H-indole-1-acetic acid;
3-(1,2-benzisothiazol-3-yl)-5-chloro-2-methyl-1H-indol-1-acetic acid;
3-(1,2-benzisothiazol-3-yl)-4-methyl-1H-indole-1-acetic acid;
3-(1,2-benzisothiazol-3-yl)-2,4-dimethyl-1H-indole-1-acetic acid;
3-(8-nitroquinolin-4-yl)-2,5-dimethyl-1H-indole-1-acetic acid
3-(8-cyano-4-quinolinyl)-2,5-dimethyl-1H-indole-1-acetic acid;
2,5-dimethyl-3-[8-(methylsulfonyl)-4-quinolinyl]-1H-indole-1-acetic acid;
2,5-dimethyl-3-(1,5-naphthyridin-4-yl)-1H-indole-1-acetic acid;
3-[8-(difluoromethoxy)-4-quinolinyl]-2,5-dimethyl-1H-indole-1-acetic acid;
5-amino-3-(7-chloro-4-quinolinyl)-2-methyl-1H-indole-1-acetic acid;
3-(7-chloro-4-quinolinyl)-2-methyl-5-[(methylsulfonyl)amino]-1H-indole-1-acetic acid;
5-(acetylamino)-3-(7-chloro-4-quinolinyl)-2-methyl-1H-indole-1-acetic acid;
3-(1,2-benzisothiazol-3-yl)-7-chloro-5-fluoro-2,4-dimethyl-1H-indol-1-yl]acetic acid;
3-(1,2-benzisothiazol-3-yl)-5-fluoro-2,4-dimethyl-1H-indol-1-yl]acetic acid;
3-(7-chloro-4-quinolin-4-yl)-5-fluoro-2,4-dimethyl-1H-indol-1-yl]acetic acid;
5-chloro-2-methyl-3-(8-quinolinyl)-1H-indole-1-acetic acid;
5-chloro-2-methyl-[3,5'-bi-1H-indole]-1-acetic acid;
3-benzo[b]thien-3-yl-5-chloro-2-methyl-1H-indole-1-acetic acid;
2,5-dimethyl-3-thieno[2,3-d]pyrimidin-4-yl 1H-indole-1-acetic acid;
5-chloro-3-(7-chloro-4-quinolinyl)-2-(hydroxymethyl)-1H-indole-1-acetic acid;
5-chloro-3-(7-chloro-4-quinolinyl)-2-(methoxymethyl)-1H-indole-1-acetic acid;
2-[(acetyloxy)methyl]-5-chloro-3-(7-chloro-4-quinolinyl)-1H-indole-1-acetic acid;
5-chloro-3-(7-chloro-4-quinolinyl)-2-[(methylamino)methyl]-1H-indole-1-acetic acid;
5-chloro-3-(7-chloro-5,8-dihydro-4-quinolinyl)-2-(1-pyrrolidinylmethyl)-1H-indole-1-acetic acid;
5-chloro-3-(7-chloro-4-quinolinyl)-2-[(methylthio)methyl]-1H-indole-1-acetic acid;
5-chloro-3-(7-chloro-4-quinolinyl)-2-[(methylsulfonyl)methyl]-1H-indole-1-acetic acid;

3-(7-chloro-4-quinolinyl)-4-methoxy-2-methyl-1H-indole-1-acetic acid;

5-chloro-2-methyl-3-[8-(trifluoromethyl)-4-quinolinyl]-1H-indole-1-acetic acid;

5-cyano-2-methyl-3-(8-methyl-4-quinolinyl)-1H-indole-1-acetic acid;

5-cyano-2-methyl-3-[8-(trifluoromethyl)-4-quinolinyl]-1H-indole-1-acetic acid;

3-(7-chloro-4-quinolinyl)-5-cyano-2-methyl-1H-indole-1-acetic acid;

3-(8-chloro-4-quinolinyl)-5-cyano-2-methyl-1H-indole-1-acetic acid;

5-cyano-2-methyl-3-(2-methyl-4-quinolinyl)-1H-indole-1-acetic acid;

3-(8-chloro-4-quinolinyl)-5-fluoro-2-methyl-1H-indole-1-acetic acid;

5-fluoro-2-methyl-3-(7-methyl-4-quinolinyl)-1H-indole-1-acetic acid;

2-methyl-5-(trifluoromethyl)-3-[8-(trifluoromethyl)-4-quinolinyl]-1H-indole-1-acetic acid;

3-(8-fluoro-4-quinolinyl)-2-methyl-5-(trifluoromethyl)-1H-indole-1-acetic acid;

3-(8-chloro-4-quinolinyl)-2-methyl-5-(trifluoromethyl)-1H-indole-1-acetic acid;

3-(8-chloro-4-quinolinyl)-2-methyl-5-(methylsulfonyl)-1H-indole-1-acetic acid;

2-methyl-3-(8-methyl-4-quinolinyl)-5-(methylsulfonyl)-1H-indole-1-acetic acid;

2-methyl-5-(methylsulfonyl)-3-[8-(trifluoromethyl)-4-quinolinyl]-1H-indole-1-acetic acid;

3-(7-chloro-4-quinolinyl)-2-methyl-5-(methylsulfonyl)-1H-indole-1-acetic acid;

5-chloro-2-methyl-3-[8-(methylsulfonyl)-4-quinolinyl]-1H-indole-1-acetic acid;

5-fluoro-2-methyl-3-[8-(methylsulfonyl)-4-quinolinyl]-1H-indole-1-acetic acid;

and pharmaceutically acceptable salts and solvates thereof.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

The compound of formula (I) above may be converted to a pharmaceutically acceptable salt or solvate thereof, preferably a basic addition salt such as sodium, potassium, calcium, aluminium, lithium, magnesium, zinc, benzathine, chloroprocaine, choline, diethanolamine, ethanolamine, ethyldiamine, meglumine, tromethamine or procaine, or an acid addition salt such as a hydrochloride, hydrobromide, phosphate, acetate, fumarate, maleate, tartrate, citrate, oxalate, methanesulphonate or p-toluenesulphonate. Preferred salts include sodium salts.

In a further aspect the invention provides a compound of formula (I) or a pharmaceutically acceptable salt or solvate thereof in the manufacture of a medicament for the treatment of diseases modulated by the CRTh2 receptor:

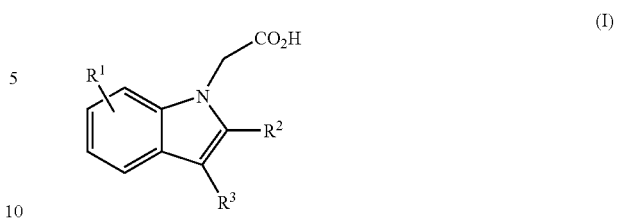

in which in which $R^1$ is hydrogen, halogen, CN, nitro, $SO_2R^4$, OH, $OR^4$, $SR^4$, $SOR^4$, $SO_2NR^5R^6$, $CONR^5R^6$, $NR^5R^6$, $NR^9SO_2R^4$, $NR^9CO_2R^4$, $NR^9COR^4$, heteroaryl, aryl (optionally substituted by chlorine or fluorine), $C_2$-$C_6$ alkenyl, $C_2$-$C_6$ alkynyl or $C_{1-6}$alkyl, the latter three groups being optionally substituted by one or more substituents independently selected from halogen, $OR^8$ and $NR^5R^6$, $S(O)_xR^7$ where x is 0, 1 or 2;

$R^2$ is hydrogen, halogen, CN, $SO_2R^4$ or $CONR^5R^6$, $CH_2OH$, $CH_2OR^4$ or $C_{1-7}$alkyl, the latter group being optionally substituted by one or more substituents independently selected from halogen atoms, $OR^8$ and $NR^5R^6$, $S(O)_xR^7$ where x is 0, 1 or 2;

$R^3$ is aryl or heteroaryl each of which is optionally substituted by one or more substituents independently selected from hydrogen, halogen, CN, nitro, OH, $SO_2R^4$, $OR^4$, $SR^4$, $SOR^4$, $SO_2NR^5R^6$, $CONR^5R^6$, $NR^5R^6$, $NR^9CO_2R^4$, $NR^9CO_2R^4$, $NR^9CO_2H$, $NR^9COR^4$, $C_2$-$C_6$ alkenyl, $C_2$-$C_6$ alkynyl, $C_{1-6}$ alkyl, the latter three groups being optionally substituted by one or more substituents independently selected from halogen atoms, $OR^8$ and $NR^5R^6$, $S(O)_xR^7$ where x=0, 1 or 2;

with the proviso that $R^3$ cannot be phenyl or substituted phenyl;

$R^4$ represents aryl, heteroaryl, or $C_{1-6}$alkyl all of which may be optionally substituted by one or more substituents independently selected from halogen atoms, aryl, heteroaryl, $OR^{10}$ and $NR^{11}R^{12}$, $S(O)_xR^{13}$ (where x=0, 1 or 2), $CONR^{14}R^{15}$, $NR^{14}COR^{15}$, $SO_2NR^{14}R^{15}$, $NR^{14}SO_2R^{15}$;

$R^5$ and $R^6$ independently represent a hydrogen atom, a $C_{1-6}$alkyl group, or an aryl, or a heteroaryl, the latter three of which may be optionally substituted by one or more substituents independently selected from halogen atoms, aryl, $OR^8$ and $NR^{14}R^{15}$, $CONR^{14}R^{15}$, $NR^{14}COR^{15}$, $SO_2NR^{14}R^{15}$, $NR^{14}SO_2R^{15}$;

or $R^5$ and $R^6$ together with the nitrogen atom to which they are attached can form a 3-8 membered saturated heterocyclic ring optionally containing one or more atoms selected from O, $S(O)_x$ where x=0, 1 or 2, $NR^{16}$, and itself optionally substituted by $C_{1-3}$ alkyl;

$R^7$ and $R^{13}$ independently represent a $C_1$-$C_6$, alkyl, an aryl or a heteroaryl group all of which maybe optionally substituted by one or more halogen atoms;

$R^8$ represents a hydrogen atom, $C(O)R^9$, $C_1$-$C_6$ alkyl an aryl or a heteroaryl group, all of which may be optionally substituted by halogen atoms or an aryl group;

each of $R^9$, $R^{10}$, $R^{11}$, $R^{12}$, $R^{14}$, $R^{15}$, independently represents a hydrogen atom, $C_1$-$C_6$ alkyl, an aryl or a heteroaryl group, all of which may be optionally substituted by a halogen atom; and $R^{16}$ is hydrogen, $C_{1-4}$ alkyl, —$COC_1$-$C_4$ alkyl, $COYC_1$-$C_4$alkyl where Y is O or $NR^7$.

Preferred groups are those defined above.

In a further aspect the invention provides a compound of formula (IA) or a pharmaceutically acceptable salt thereof:

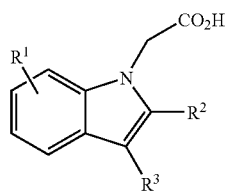

(IA)

in which $R^1$ is one or more substituents independently selected from halogen, CN, nitro, $SO_2R^4$, $OR^4$, $SR^4$, $SOR^4$, $SO_2NR^5R^6$, $CONR^5R^6$, $NR^5R^6$, $NR^7SO_2R^4$, $NR^7CO_2R^4$, $C_2$-$C_6$ alkenyl, $C_2$-$C_6$ alkynyl or $C_{1-6}$alkyl, the latter three groups being optionally substituted by one or more substituents independently selected from halogen, $OR^7$ and $NR^8R^9$, $S(O)_xR^7$ where x is 0, 1 or 2;

$R^2$ is hydrogen, halogen, CN, $SO_2R^4$ or $CONR^5R^6$, $COR^4$ or $C_{1-7}$alkyl, the latter group being optionally substituted by one or more substituents independently selected from halogen atoms, $OR^7$ and $NR^8R^9$, $S(O)_xR^7$ where x is 0, 1 or 2;

$R^3$ is aryl or heteroaryl each of which is optionally substituted by one or more substituents independently selected from halogen, CN, nitro, $SO_2R^4$, $OR^4$, $SR^4$, $SOR^4$, $SO_2NR^5R^6$, $CONR^5R^6$, $NR^5R^6$, $NR^7SO_2R^4$, $NR^7CO_2R^4$, $C_2$-$C_6$ alkenyl, $C_2$-$C_6$ alkynyl, $C_{1-6}$ alkyl, the latter three groups being optionally substituted by one or more substituents independently selected from halogen atoms, $OR^7$ and $NR^8R^9$, $S(O)_xR^7$ where x=0, 1 or 2;

with the proviso that $R^3$ cannot be phenyl;

$R^4$ represents hydrogen or $C_{1-6}$alkyl which may be optionally substituted by one or more substituents independently selected from halogen atoms, aryl, heteroaryl, $OR^{10}$ and $NR^{11}R^{12}$ $S(O)_x R^{13}$ (where x=0, 1 or 2), $CONR^{14}R^{15}$, $NR^{14}COR^{15}$, $SO_2NR^{14}R^{15}$, $NR^{14}SO_2R^{15}$;

$R^5$ and $R^6$ independently represent a hydrogen atom, a $C_{1-6}$alkyl group, or an aryl, or a heteroaryl, the latter three of which may be optionally substituted by one or more substituents independently selected from halogen atoms, aryl, $OR^{13}$ and $NR^{14}R^{15}$, $CONR^{14}R^{15}$, $NR^{14}COR^{15}$, $SO_2NR^{14}R^{15}$, $NR^{14}SO_2R^{15}$;

or $R^5$ and $R^6$ together with the nitrogen atom to which they are attached can form a 3-8 membered saturated heterocylic ring optionally containing one or more atoms selected from O, $S(O)_x$ where x=0, 1 or 2, $NR^{16}$, and itself optionally substituted by $C_{1-3}$ alkyl;

each of $R^7$, $R^8$, $R^9$ $R^{10}$, $R^{11}$, $R^{12}$, $R^{13}$, $R^{14}$, $R^{15}$, independently represents a hydrogen atom, $C_1$-$C_6$, alkyl, an aryl or a heteroaryl group; and $R^{16}$ is hydrogen, $C_{1-4}$ alkyl, —$COC_1$-$C_4$ alkyl, $COYC_1$-$C_4$alkyl, Y is O or $NR^7$.

In a further aspect the invention provides a process for the preparation of a compound of formula (I)/(IA) which comprises reaction of a compound of formula (II):

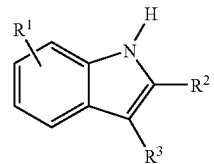

(II)

in which $R^1$, $R^2$ and $R^3$ are as defined in formula (I) or are protected derivatives thereof, with a compound of formula (III):

 L—$CH_2CO_2R^{17}$ (III)

where $R^{17}$ is an alkyl group and L is a leaving group in the presence of a base, and optionally thereafter in any order:

removing any protecting group hydrolysing the ester group $R^{17}$ to the corresponding acid forming a pharmaceutically acceptable salt.

The reaction can be carried out in a suitable solvent such as THF using a base such as sodium hydride, caesium carbonate or the like. Suitable groups $R^{17}$ include $C_{1-6}$ alkyl groups such as methyl, ethyl or tertiary butyl. Suitable L is a leaving group such as halo, in particular bromo or chloro. Preferably the compound of formula (III) is ethyl bromoacetate.

Hydrolysis of the ester group $R^{17}$ can be carried out using routine procedures, for example by stirring with aqueous sodium hydroxide.

Compounds of formula (II) can be prepared by reacting a compound of formula (IV):

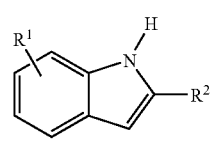

(IV)

in which $R^1$ and $R^2$ are as defined in formula (I) or are protected derivatives thereof, with a base and a compound of formula (V):

 $R^3$—$L^2$ (V)

in which $R^3$ is as defined in formula (I) or is a protected derivative thereof, and $L^2$ is a leaving group, and optionally thereafter removing any protecting groups.

Suitable bases are those which will de-protonate the indole, including Grignard reagents such as ethylmagnesium bromide. The reaction is carried out in an inert nitrogen atmosphere in a solvent such as THF. Suitable $L^2$ is halogen, for example chloro.

Or compounds of formula (II) can be prepared by heating a compound of formula (IV) with a compound of formula (V). The reaction can be carried out in an inert atmosphere in a solvent such as DMF or NMP and optionally thereafter removing any protecting groups.

Compounds of formula (II) can be prepared from compounds of formula (VI).

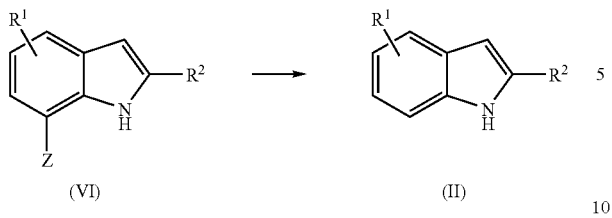

In which Z is a halogen atom, preferably chlorine or bromine in which $R^1$ and $R^2$ or protected derivatives thereof are as defined in formula (I).

The reaction is carried out under a hydrogen atmosphere in the presence of a catalyst, preferably palladium on charcoal in a solvent, such as ethanol.

Compounds of formula (VI) can be prepared by reaction with compounds of formula (VII) with compounds of formula (VIII).

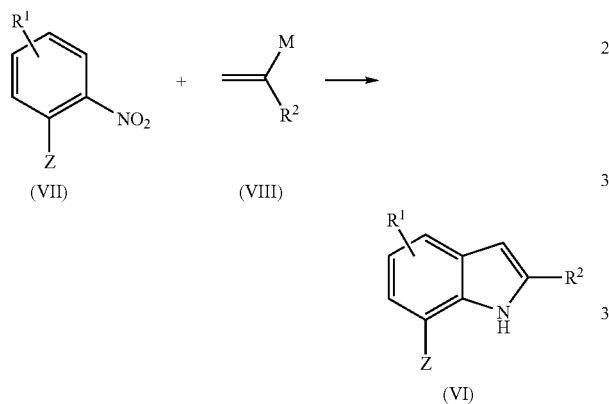

The reaction is carried out at −40° C. in a suitable solvent such as THF. M is a metal halide such as magnesium bromide, $R^1$ and $R^2$ are as described in formula (I) or protected derivatives thereof. Some compounds of formulae (IV), (V), (VII) and (VIII) are commercially available or can be prepared using standard chemistry well known in the art.

Alternatively compounds of formula (IV) can be prepared by reacting a compound of formula (IX) with a thiol in acidic conditions, such as thiosalycilic acid and trifluoroacetic acid

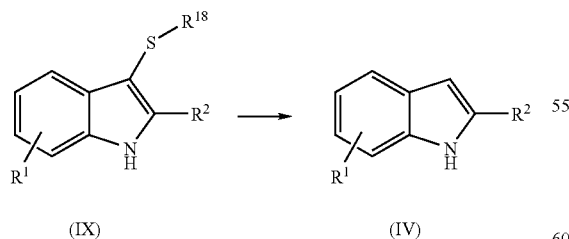

where $R^1$ and $R^2$ are as described in formula (I) or protected derivatives thereof and $R^{18}$ is alkyl or substituted aryl, preferably $R^{18}$ is 4-chlorophenyl or methyl.

Compounds of formula (IX) can be prepared by reacting a compound of formula (X) with a compound of formula (XI).

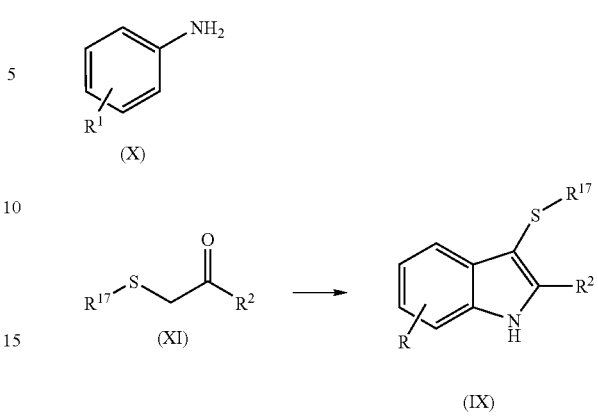

The reaction can be carried out in the presence of a chlorinating agent. Preferably the reaction is carried out using sulfonyl chloride or tert-butyl hypochlorite in a solvent such as dichloromethane or THF.[1]

Or, compounds of formula (IX) can be prepared by reacting a compound of formula (XI) with a compound of formula (VII).

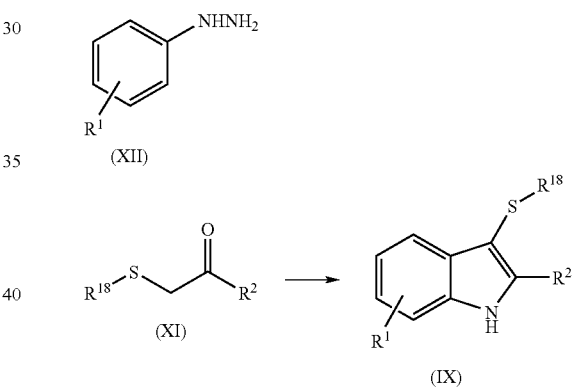

The reaction is carried out in a suitable solvent such as acetonitrile.

Compounds of formulae (X), (XI) and (XII) are commercially available or can be prepared is using methods well known in the art, in which $R^1$ and $R^2$ or protected derivatives thereof are as defined in formula (I).

Compounds of formula (I) can also be prepared from compounds of formula (XI) with a compound of formula (XIV).

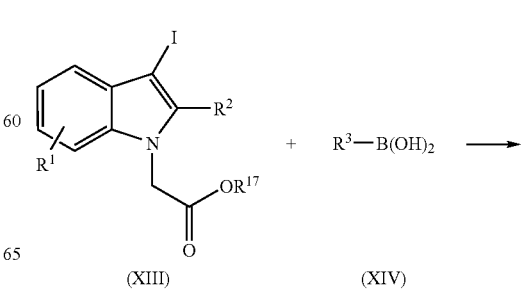

-continued

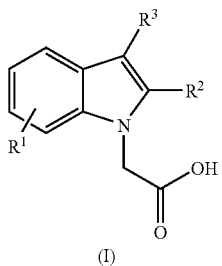

The reaction is carried out using a palladium catalyst with a suitable ligand, such as tri(o-tolyl) phosphine in an organic solvent. A compound of formula (I) is obtained directly as described or the corresponding ester is obtained, which can be hydrolysed as outlined above.

Or, certain compounds of formula (I) can be prepared by reaction of compounds of formula (XV) with a suitable nucleophile, for example alkoxy or amino.

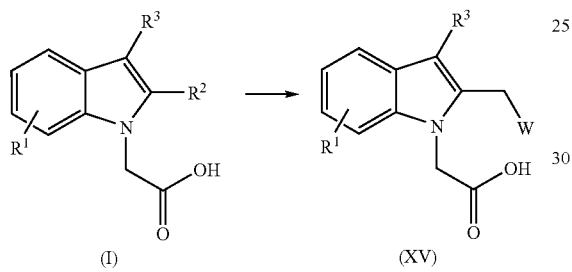

in which $R^1$ and $R^2$ or protected derivatives thereof are as defined in formula (I). W is a halogen atom, preferably bromine or chlorine.

Compounds of formula (XV) are prepared from compounds of formula (I) where $R^2$ is methyl.

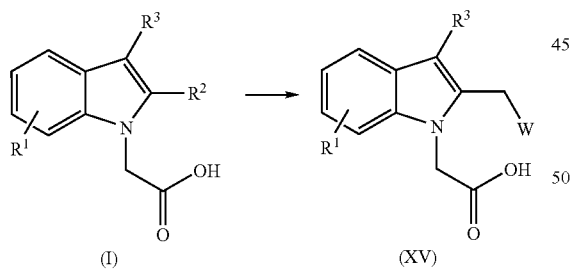

Certain compounds of formulae (IV), (VI), (VII), (VI), (IX), (XIII) and (XV) or protected derivatives thereof are believed to be novel and form a further aspect of the invention.

It will be appreciated by those skilled in the art that in the processes of the present invention certain functional groups in the starting reagents or intermediate compound may need to be protected by protecting groups. Thus, the preparation of the compound of formula (I) may involve, at an appropriate stage, the removal of one or more protecting groups. The protection and deportation of functional groups is fully described in 'Protective Groups in Organic Chemistry', edited by J. W. F. McOmie, Plenum Press (1973), and 'Protective Groups in Organic Synthesis', 3rd edition, T. W. Greene & P. G. M. Wuts, Wiley-Interscience (1999).

In a further aspect, the present invention provides the use of a compound of formula (I), pharmaceutically acceptable salt or solvate thereof for use in therapy.

The compounds of formula (I) have activity as pharmaceuticals, in particular as modulators of CRTh2 receptor activity, and may be used in the treatment (therapeutic or prophylactic) of conditions/diseases in human and non-human animals which are exacerbated or caused by excessive or unregulated production of $PGD_2$ and its metabolites. Examples of such conditions/diseases include:

(1) (the respiratory tract) obstructive airways diseases including: asthma (such as bronchial, allergic, intrinsic, extrinsic and dust asthma particularly chronic or inveterate asthma (e.g. late asthma and airways hyper-responsiveness)); chronic obstructive pulmonary disease (COPD)(such as irreversible COPD); bronchitis (including eosinophilic bronchitis); acute, allergic, atrophic rhinitis or chronic rhinitis (such as rhinitis caseosa, hypertrophic rhinitis, rhinitis purulenta, rhinitis sicca), rhinitis medicamentosa, membranous rhinitis (including croupous, fibrinous and pseudomembranous rhinitis), scrofoulous rhinitis, perennial allergic rhinitis, seasonal rhinitis (including rhinitis nervosa (hay fever) and vasomotor rhinitis); nasal polyposis; sarcoidosis; farmer's lung and related diseases; fibroid lung; idiopathic interstitial pneumonia; cystic fibrosis; antitussive activity; treatment of chronic cough associated with inflammation or iatrogenic induced;

(2) (bone and joints) arthrides including rheumatic, infectious, autoimmune, seronegative, spondyloarthropathies (such as ankylosing spondylitis, psoriatic arthritis and Reiter's disease), Behcet's disease, Sjogren's syndrome and systemic sclerosis;

(3) (skin and eyes) psoriasis, atopical dermatitis, contact dermatitis, other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, chronic skin ulcers, uveitis, Alopecia areatacorneal ulcer and vernal conjunctivitis;

(4) (gastrointestinal tract) Coeliac disease, proctitis, eosinopilic gastro-enteritis, mastocytosis, Crohn's disease, ulcerative colitis, irritable bowel disease; food-related allergies which have effects remote from the gut, (such as migraine, rhinitis and eczema);

(5) (central and peripheral nervous system) Neurodegenerative diseases and dementia disorders (such as Alzheimer's disease, amyotrophic lateral sclerosis and other motor neuron diseases, Creutzfeldt-Jacob's disease and other prion diseases, HIV encephalopathy (AIDS dementia complex), Huntington's disease, frontotemporal dementia, Lewy body dementia and vascular dementia), polyneuropathies (such as Guillain-Barré syndrome, chronic inflammatory demyelinating polyradiculoneuropathy, multifocal motor neuropathy), plexopathies, CNS demyelination (such as multiple sclerosis, acute disseminated/haemorrhagic encephalomyelitis, and subacute sclerosing panencephalitis), neuromuscular disorders (such as myasthenia gravis and Lambert-Eaton syndrome), spinal disorders (such as tropical spastic paraparesis, and stiff-man syndrome), paraneoplastic syndromes (such as cerebellar degeneration and encephalomyelitis), CNS trauma, migraine and stroke.

(6) (other tissues and systemic disease) atherosclerosis, Acquired Immunodeficiency Syndrome (AIDS), lupus erythematosus; systemic lupus, erythematosus; Hashimoto's thyroiditis, type I diabetes, nephrotic syndrome, eosinophilia fascitis, hyper IgE syndrome, lepromatous leprosy, idiopathic thrombocytopenia pupura; post-operative adhesions, sepsis and ischemic/reperfusion injury in the heart, brain, peripheral limbs hepatitis (alcoholic, steatohepatitis and chronic viral), glomerulonephritis, renal impairment, chronic renal failure and other organs (7) (allograft rejection) acute and chronic following, for example, transplantation of kidney, heart, liver, lung, bone marrow, skin and cornea; and chronic graft versus host disease;

(8) Diseases associated with raised levels of $PGD_2$ or its metabolites.

Thus, the present invention provides a compound of formula (I), or a pharmaceutically-acceptable salt or solvate thereof, as hereinbefore defined for use in therapy.

Preferably the compounds of the invention are used to treat diseases in which the chemokine receptor belongs to the CRTh2 receptor subfamily.

Particular conditions which can be treated with the compounds of the invention are asthma, rhinitis and other diseases in which raised levels of $PGD_2$ or its metabolites. It is preferred that the compounds of the invention are used to treat asthma.

In a further aspect, the present invention provides the use of a compound of formula (I), or a pharmaceutically acceptable salt or solvate thereof, as hereinbefore defined in the manufacture of a medicament for use in therapy.

In a further aspect, the present invention provides the use of a compound or formula (I), or a pharmaceutically acceptable salt or solvate thereof, as hereinbefore defined in the manufacture of a medicament for use in therapy in combination with drugs used to treat asthma and rhinitis (such as inhaled and oral steroids, inhaled β2-receptor agonists and oral leukotriene receptor antagonists).

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of CRTh2 receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating diseases mediated by PGD2 or its metabolites wherein the prostanoid binds to its receptor (especially CRTh2) receptor, which comprises administering to a patient a therapeutically effective amount of a compound of formula (I), or a pharmaceutically acceptable salt, solvate or prodrug thereof, as hereinbefore defined.

The invention also provides a method of treating an inflammatory disease, especially psoriasis, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

For the above-mentioned therapeutic uses the dosage administered will, of course, vary with the compound employed, the mode of administration, the treatment desired and the disorder indicated.

The compound of formula (I), prodrugs and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as herein before defined, in association with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compound of the invention is administered orally.

The invention will now be illustrated by the following non-limiting examples in which, unless stated otherwise:

The invention will now be illustrated by the following non-limiting examples in which, unless stated otherwise:

(i) the title and sub-titled compounds of the examples and methods were named using the ACD labs/name program (version 6.0) from Advanced Chemical Development Inc, Canada;

(ii) unless stated otherwise, reverse phase preparative HPLC was conducted using a Symmetry, NovaPak or Ex-Terra reverse phase silica column;

(iii) Flash column chromatography refers to normal phase silica chromatography;

(iv) solvents were dried with $MgSO_4$ or $Na_2SO_4$;

(v) Evaporations were carried out by rotary evaporation in vacuo and work-up procedures were carried out after removal of residual solids such as drying agents by filtration;

(vi) Unless otherwise stated, operations were carried out at ambient temperature, that is in the range 18-25° C. and under an atmosphere of an inert gas such as argon or nitrogen;

(vii) yields are given for illustration only and are not necessarily the maximum attainable;

(viii) the structures of the end-products of the formula (I) were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(ix) intermediates were not generally fully characterised and purity was assessed by thin layer chromatography (TLC), high-performance liquid chromatography (HPLC), mass spectrometry (MS), infra-red (IR) or NMR analysis;

(x) mass spectra (MS): generally only ions which indicate the parent mass are reported when given, $^1$H NMR data is quoted in the form of delta values for major diagnostic protons, given in parts per million (ppm) relative to tetramethylsilane (TMS) as an internal standard;

(xi) the following abbreviations are used:

EtOAc Ethylacetate
DMF N,N-Dimethyl formamide
NMP N-methylpyrrolidine
THF tetrahydrofuran
RT room temperature
TFA trifluoroacetic acid
H hour

EXAMPLE 1

3-(2-chloro-4-quinolinyl)-2,5-dimethyl-1H-indole-1-acetic acid a) 7-chloro-4-(2,5-dimethyl-1H-indol-3-yl)quinoline 2,5-dimethylindole (500 mg) was dissolved in dry toluene (2 ml), and maintained under a nitrogen atmosphere. The reaction was cooled to 0° C. before adding EtMgBr (2.5 ml, 3M in Et$_2$O) dropwise, keeping the temperature below 5° C. Allowed the mixture to warm to RT and stirred for 0.5 h. A solution of 4,7-dichloroquinoline (680 mg) in dry THF (3 ml) was added slowly to the reaction. After stirring for 30 minutes at RT the reaction was slowly heated to 90° C. and stirred overnight. The reaction was allowed to cool to RT before adding EtOAc and water to the mixture. The organic layer was separated and the organic layer was extracted with EtOAc (×3). The combined organics were washed with saturated aqueous NH$_4$Cl, H$_2$O and brine then dried (Na$_2$SO$_4$) and the solvent was evaporated under reduced pressure. Purification by chromatography eluting with 15% acetone/isohexane gave the sub-title compound (0.47 g).

MS: ESI (+ve): 307 (M+1, 100%)

b) 3-(2-chloro-4-quinolinyl)-2,5-dimethyl-1H-indole-1-acetic acid 7-chloro-4-(2,5-dimethyl-1H-indol-3-yl)quinoline (370 mg) was dissolved in dry THF (8 ml), and maintained under a nitrogen atmosphere. The reaction was cooled to −5° C. before slowly adding NaH (53 mg, 60% dispersion in mineral oil) portion-wise. Allowed the mixture to warm to RT and stirred for 40 minutes. The mixture was cooled to 0° C. before adding ethyl bromoacetate (0.147 ml) dropwise. After stirring for 1 hour at 15° C., the reaction was diluted with EtOH (5 ml) and 10% aqueous NaOH solution (3 ml). Stirring over night at RT converted the ethyl ester to the acid. Acidified with 1M aqueous HCl and extracted with EtOAc (×3). The combined organics were washed with water and brine then dried (Na$_2$SO$_4$) and the solvent was evaporated under reduced pressure. Further purification was by solid phase extraction using NH$_2$ sorbent (6.5 g), eluting CH$_3$CN and 20% AcOH/CH$_3$CN. The solvent was evaporated under reduced pressure and the residue was azeotroped using toluene. This gave the title compound (378 mg).

MS: ESI (+ve): 366 (M+1) $^1$H NMR (DMSO-d6) δ 8.97 (1H, d), 8.14 (1H, d), 7.77 (1H, d), 7.56 (1H, dd), 7.49 (1H, d), 7.33 (1H, d), 6.99-6.92 (2H, m), 4.47 (2H, m), 2.29 (3H, s), 2.21 (3H, s).

EXAMPLE 2

3-(2-chloro-4-quinolinyl)-2-methyl-1H-indole-1-acetic acid

The title compound was prepared in an analogous method as for preparation of Example 1.

MS: ESI (+ve): 351 (M+1). $^1$H NMR (DMSO-d6) δ 9.14 (1H, d), 8.30 (1H, d), 7.89 (1H, d), 7.79-7.72 (2H, m), 7.59 (1H, d), 7.27-7.19 (2H, m), 7.12-7.06 (1H, m), 5.18 (2H, s), 2.32 (3H, s).

EXAMPLE 3

3-(2-chloro-4-quinolinyl)-1H-indole-1-acetic acid

The title compound was prepared in an analogous method as for preparation of Example 1.

MS: ESI (+ve): 337 (M+1). $^1$H NMR (DMSO) δ 8.21 (1H, d), 8.14 (1H, m), 7.86 (1H, s), 7.61-7.66 (2H, m), 7.56 (2H, d), 7.24-7.30 (m, 1H), 7.12-7.19 (1H, m) and 5.12 (3H, s).

EXAMPLE 4

2-methyl-3-(4-quinolinyl)-1H-indole-1-acetic acid

The title compound was prepared in an analogous method as for preparation of Example 1.

MS: ESI (+ve): 317 (M+1). $^1$H NMR DMSO δ 8.97 (1H, d), 8.11 (1H, d), 7.70-7.82 (2H, m), 7.45-7.57 (3H, m), 7.09-7.22 (2H, m), 6.99-7.07 (1H, m), 5.13 (2H, s), 2.26 (3H, s).

EXAMPLE 5

3-(2-chloro-4-quinolinyl)-5-methoxy-2-methyl-1H-indole-1-acetic acid

The title compound was prepared in an analogous method as for preparation of Example 1.

MS: APCI (M+H): 381 $^1$H NMR (DMSO-d6) δ 8.99 (1H, d), 8.16 (1H, d), 7.76 (1H, d), 7.63-7.56 (m, 1H), 7.52 (1H, d), 7.45 (1H, d), 6.81 (1H, dd), 6.61 (1H, d), 5.07 (2H, s), 3.62 (3H, s) and 2.22 (3H, s).

EXAMPLE 6

3-(2-chloro-4-quinolinyl)-2,6-dimethyl-1H-indole-1-acetic acid

The title compound was prepared in an analogous method as for preparation of Example 1.

MS: APCI (M+H): 365 $^1$H NMR DMSO-d6) δ 8.99 (1H, d), 8.18 (1H, d), 7.77 (1H, d), 7.59 (1H, dd), 7.50 (1H, d), 7.36 (1H, d), 7.02 (1H, d), 6.85 (1H, d), 5.06 (2H, s), 2.42 (3H, s) and 2.24 (3H, s).

EXAMPLE 7

3-(2-chloro-4-quinolinyl)-2,4-dimethyl-1H-indole-1-acetic acid

The title compound was prepared in an analogous method as for preparation of Example 1.

MS: APCI [M+H]$^+$: 365 $^1$H NMR (DMSO-d6) δ 8.97 (1H, d), 8.13 (1H, d), 7.50-7.61 (2H, m), 7.47 (1H, d), 7.24 (1H, d), 6.95-7.02 (1H, m), 6.70 (1H, d), 4.63 (2H, s), 2.05 (3H, s) and 1.74 (3H, d).

EXAMPLE 8

3-(2-benzothiazolyl)-2,5-dimethyl-1H-indole-1-acetic acid

The title compound was prepared in an analogous method as for preparation of Example 1 using 2-chloro-1,3-benzothiazole.

MS: ESI (−ve) 321 (M−1)

EXAMPLE 9

2,5-dimethyl-3-(7-methyl-4-(quinolinyl)-1H-indole-1-acetic acid a) 4-(2,5-dimethyl-1H-indol-3-yl)-7-methyl-quinoline The sub-title compound was prepared by the method of Example 1 step a) using 2,5-dimethyl indole and 4-chloro-7-methyl-quinoline.

$^1$H NMR DMSO δ 11.34 (1H, s), 7.99 (1H, dd), 7.70 (2H, ddd), 7.46-7.4 (1H, m), 7.35 (1H, s), 7.28 (1H, s), 6.92 (1H, dd), 6.89 (1H, s), 2.72 (3H, s), 2.27 (3H, s).

b) 2,5-dimethyl-3-(7-methyl-4-quinolinyl)-1H-indole-1-acetic acid, ethyl ester

The title compound was prepared by the method of Example 1 step b) using the product of step a).

MS: ESI (+ve) 344 [M+H]$^+$ $^1$H NMR (DMSO-d6) δ 7.99 (1H, dd), 7.72-7.68 (1H, m), 7.66 (1H, d), 7.43 (1H, dd), 7.38 (1H, d), 6.97 (1H, d), 6.92 (1H, s), 5.00 (2H, s), 2.71 (3H, s), 2.29 (3H, s) and 2.21 (3H, s).

EXAMPLE 10

2,5-dimethyl-3-(8-methyl-4-quinolinyl)-1H-indole-1-acetic acids sodium salt a) 8-Methyl-(2,5-dimethyl-1H-indol-3-yl)quinoline 2,5-Dimethylindole (290 mg) and 8-methyl-4-chloroquinoline (360 mg) were suspended in N-methylpyrolidinone (0.5 ml), and maintained under a nitrogen atmosphere. The reaction was heated to 140° C. with stirring for 45 minutes. On cooling a deep red precipitate formed, the mixture was diluted with diethylether and the solid collected by filtration, and dried to give the sub-title compound (570 mg).

MS: ESI (+ve): 287 [M+H]$^+$ b) Ethyl [3-(8-Methyl-4-quinolinyl)-2,5-dimethyl-1H-indole-1-acetate 8-Methyl-4-(2,5-dimethyl-1H-indol-3-yl)quinoline (0.57 g) and caesium carbonate (1.28 g) were suspended in dry acetone (100 ml), followed by addition of ethyl bromoacetate (0.37 g) and maintained under a nitrogen atmosphere. The reaction was heated to reflux for 24 h. Further quantities of caesium carbonate (0.64 g) and ethyl bromoacetate (0.19 g) were required to complete the reaction after a further 6 hours. The solvents were evaporated under reduced pressure and the residue purified by silica flash chromatography using 8:1 isohexane/acetone as eluent to give the sub-title compound (35 mg).

MS: ESI (+ve): 373 [M+H]$^+$ c) 2,5-Dimethyl-3-(8-methyl-4-quinolinyl)-1H-indole-1-acetic acid, monosodium salt The product obtained from Step b (0.30 g) was suspended in methanol (20 ml) and to it added 1.0M sodium hydroxide (0.81 ml) for the mixture to be stirred overnight at room temperature to complete the reaction. The solution was evaporated to dryness and triturated with diethyl ether to give an off-white solid which was collected by filtration and is dried under vacuum at 40° C. overnight (0.30 g) to give the title compound.

MS: ESI (+ve): 345 [M+H]$^+$ $^1$H NMR (DMSO-d6) δ 8.95 (1H, d), 7.62 (2H, t), 7.46-7.34 (2H, m), 7.24 (1H, d), 6.93-6.88 (2H, m), 4.46 (2H, d), 2.79 (3H, s), 2.28 (3H, s), 2.20 (3H, s)

EXAMPLE 11

3-(6-fluoro-4-quinolinyl)-2,5-dimethyl-1H-indole-1-acetic acid, sodium salt a) 6-Fluoro-4-(2,5-dimethyl-1H-indol-3-yl)quinoline The sub-title compound was prepared by the method of Example 10 part a, using 2,5-dimethyl indole and 4-chloro-6-fluoroquinoline.

MS: ESI (+ve): 291 [M+H]$^+$ b) Ethyl [3-(6-Fluoroquinolin-4-yl)-2,5-dimethyl-1H-indol-1-yl]acetate The sub-title compound was prepared by the method of Example 10 part b, using the product of part a.

MS: ESI (+ve): 377 [M+H]$^+$ c) 3-(6-Fluoro-4-quinolinyl)-2,5-dimethyl-1H-indole-1-acetic acid, sodium salt The title compound was prepared by the method of Example 10 part c, using the product of part b.

MS: ESI (+ve): 349 [M+H]$^+$ $^1$H NMR (DMSO-d6) δ 8.93 (1H, d), 8.16 (1H, dd), 7.69 (1H, td), 7.48 (1H, d), 7.41 (1H, dd), 7.26 (1H, d), 6.96-6.91 (2H, m), 4.45 (2H, s), 2.30 (3H, s), 2.21 (3H, s)

EXAMPLE 12

3-(1-isoquinolinyl)-2,5-dimethyl-1H-indole-1-acetic acid, sodium salt a) 1-(2,5-Dimethylindol-3-yl)isoquinoline The sub-title compound was prepared by the method of Example 10 part a, using 2,5-dimethyl indole and 1-chloroisoquinoline.

MS: ESI (+ve): 273 [M+H]$^+$ b) Ethyl [2,5-dimethyl-3-(isoquinolin-1-yl)-1H-indol-1-yl]acetate The sub-title compound was prepared by the method of Example 10 part b, using the product of part a.

MS: ESI (+ve): 359 [M+H]$^+$ c) 3-(1-isoquinolinyl)-2,5-dimethyl-1H-indole-1-acetic acid, monosodium salt The title compound was prepared by the method of Example 10 part c, using the product of part b.

MS: ESI (+ve): 331 [M+H]$^+$ $^1$H NMR (DMSO-d6) δ 8.60 (1H, d), 8.01 (1H, d), 7.91 (1H, d), 7.75 (2H, dd), 7.55 (1H, dd), 7.23 (1H, d), 6.95 (1H, s), 6.89 (2H, dd), 4.46 (2H, q), 2.27 (3H, s), 2.24 (3H, s).

EXAMPLE 13

3-(6-Methoxy-2-methyl-4-quinolinyl)-2,5-dimethyl-1H-indole-1-acetic acid, sodium salt a) 6-Methoxy-2-methyl-4-(2,5-dimethyl-1H-indol-3-yl)quinoline The sub-title compound was prepared by the method of Example 10 part a, using 2,5-dimethyl indole and 4-chloro-6-methoxy-2-methylquinoline.

MS: ESI (+ve): 317 [M+H]$^+$ b) Ethyl [3-(6-methoxy-2-methyl-4-quinolinyl)-2,5-dimethyl-1H-indole-1]acetate The sub-title compound was prepared by the method of Example 10 part b, using the product of part a.
MS: ESI (+ve): 403 [M+H]+ c) 3-(6-methoxy-2-methyl-4-quinolinyl)-2,5-dimethyl-1H-indole-1-acetic acid monosodium salt The title compound was prepared by the method of Example 10 part c, using the product of part b.
MS: ESI (+ve): 375 [M+H]+ 1H NMR (DMSO-d6) δ 7.89 (1H, d), 7.35 (1H, dd), 7.29 (1H, s), 7.25 (1H, d), 7.11 (1H, d), 6.99 (1H, s), 6.91 (1H, dd), 4.45 (2H, q), 3.65 (3H, s), 2.65 (3H, d), 2.32 (3H, d), 2.22 (3H, s)

EXAMPLE 14

2,5-dimethyl-3-(4-quinolinyl)-1H-indole-1-acetic acid, sodium salt

The product from Example 10, step c) (24 mg) was suspended in ethanol (50 ml) and triethylamine (1 ml) and hydrogenated at 1.5 bar in the presence of 10% palladium on charcoal (24 mg) overnight. The mixture was filtered through celite and the filtrate evaporated and the resultant precipitate triturated with diethyl ether to give the title compound as a yellow powder (90 mg).
MS: ESI (+ve): 331 [M+H]+ 1H NMR (DMSO-d6) δ 8.94 (1H, d), 8.09 (1H, d), 7.76 (2H, m), 7.52 (1H, t), 7.45 (1H, d), 7.33 (1H, d), 6.94 (2H, d), 4.77 (2H, s), 2.26 (3H, d), 2.23 (3H, d)

EXAMPLE 15

2,5-Dimethyl-3-[8-(trifluoromethyl)-4-quinolinyl]-1H-indole-1-acetic acid, sodium salt a) 4-(2,5-Dimethyl-1H-indol-3-yl)-8-(trifluoromethyl)-quinoline, hydrochloride A mixture of 2,5-dimethylindole (765 mg) and 4-chloro-8-trifluoromethylquinoline (1.22 g) in NMP (1.5 ml) and 4M HCl in dioxane (0.2 ml) was heated at 140° C. for 1 h. After cooling the mixture was triturated with ether and filtered to give the sub-title compound (1.33 g) as a dark red solid.
MS: ESI (+ve): 341 [M+H]+ 100%

Alternative Method

A solution of 2,5-dimethylindole (675 mg) in dioxane (1.5 ml) was added to a solution of 4-chloro-8-trifluoromethylquinoline (1.08 g) in 2M HCl in dioxane (2.2 ml) at 80° C. and the resultant solution was heated at 100° C. for 1 h. After cooling the mixture was diluted with ether and the precipitate was collected to give the sub-title compound (1.44 g), identical to that prepared above.

b) Ethyl 2,5-dimethyl-3-[8-(trifluoromethyl)-4-quinolinyl]-1H-indole-1-acetate

A mixture of the product from step a) (1.74 g), ethyl bromoacetate (0.62 ml) and caesium carbonate (3.15 g) in dry acetone (45 ml) was heated under reflux under nitrogen for 32 hours. Water and aq. ammonium chloride solution were added and the mixture was extracted with ethyl acetate. The organic extracts were dried (MgSO4), evaporated and purified by chromatography (silica, petrol-acetone as eluent) to give the sub-title compound (1.63 g).
MS: ESI (+ve): 427 [M+H]+ 100% c) 2,5-Dimethyl-3-[8-(trifluoromethyl)-4-quinolinyl]-1H-indole-1-acetic acid

A solution of product from step b) (1.46 g) and 1 M sodium hydroxide (3.42 ml) in THF (20 ml) and methanol (2 ml) was stirred for 16 hours. The solvent was removed in vacuo and the residue was dissolved in water (20 ml) and washed with dichloromethane. 1M HCl (3.4 ml) was added slowly to the stirred solution. The precipitate was collected and dried to give the title compound (1.23 g. M.p. 145° C.
MS: ESI (+ve): 399 [M+H]+100% 1H NMR (DMSO-d6) δ 2.24 (3H, s), 9.11 (1H, d), 8.21 (1H, d), 8.02 (1H, d), 7.67 (1H, t) 7.63 (1H, d), 7.44 (1H, d), 7.01 (1H, d), 6.95 (1H, s), 5.12 (2H, s), 2.31 (3H, d).

EXAMPLE 16

3-(2-benzoxazolyl)-2,5-dimethyl-1H-indole-1-acetic acid a) 2-(2,5-dimethyl-1H-indol-3-yl)-benzoxazole 2,5-dimethyl indole (0.3 g), 2-chlorooxazole (0.47 g) and NMP (2 ml) were heated in a microwave at 100 watts for 20 min at 160° C. Water and EtOAc were added and separated, the aqueous phase was re-extracted with EtOAc (×4). The combined organic extracts were dried (MgSO4) and concentrated in vacuo. The precipitate was triturated with EtOAc then recrystallised from methanol to give the title compound (0.19 g).
MS: ESI (+ve): 263 [M+H]+
Where is reaction b)?

c) 3-(2-benzoxazolyl)-2,5-dimethyl-1H-indole-1-acetic acid
The title compound was prepared by the method of Example 1 part b, using the product of step a).
1H NMR (DMSO-d6) δ 8.15 (1H, s), 7.78-7.63 (2H, m), 7.39-7.22 (3H, m), 7.0 (1H, d), 4.5 (2H, s), 2.83 (3H, s) and 2.81 (3H, s).

EXAMPLE 17

3-(1,2-Benzisothiazol-3-yl)-2,5-dimethyl-1H-indole-1-acetic acid, sodium salt a) 3-(2,5-dimethyl-1H-indol-3-yl)-1,2-benzisothiazole
The sub-title compound was prepared by the method of Example 10 part a, using 2,5-dimethyl indole and 3-chloro-1,2-benzisothiazole.
MS: ESI (+ve): 279 [M+H]+ b) Ethyl 3-(1,2-benzisothiazol-3-yl)-2,5-dimethyl-1H-indole-1-acetate
The sub-title compound was prepared by the method of Example 10 part b.
MS: ESI (+ve): 365 [M+H]+ c) 3-(1,2-benzisothiazol-3-yl)-2,5-dimethyl-1H-indole-1-acetic acid
The sub-title compound was prepared by the method of Example 10 part c, using the product of step b).
1H NMR (DMSO-d6) δ 8.3 (1H, d), 7.8 (1H, d), 7.6 (1H, d), 7.5 (1H, t), 7.3 (1H, d), 7.25 (1H, s), 6.95 (1H, d), 2.4 (3H, s), 2.32 (3H, s).

EXAMLE 18

3-(7-chloro-4-quinolinyl)-2,5-dimethyl-6-(methylsulfonyl)-1H-indole-1-acetic acid a) 7-chloro-4-[2,5-dimethyl-6-(methylsulfonyl)-1H-indol-3-yl]-quinoline
Trifluoroacetic anhydride (few drops) and methane sulfonic anhydride (0.114 ml×3) were added to the product of Example 1 part a) in a sealed tube, and heated to 100° C. for 6 hours and then 24 hours. The residue was passed through silica eluting with MeOH/dichloromethane (9:1 v/v). This was further purified by RPHPLC eluting with acetonitrile/ammonium acetate (25/75 to 95/05) to give the sub-title compound (66 mg).

MS: ESI (−ve): 383 [M−H]⁻ b) 3-(7-chloro-4-quinolinyl)-2,5-dimethyl-6-(methylsulfonyl)-1H-indole-1-acetic acid The title compound was prepared by the method of Example 1 part b) using the product of step a).

$^1$H NMR (DMSO-d6) δ 9.01 (1H, d), 8.17 (1H, d), 7.96 (1H, d), 7.72 (1H, d), 7.56-7.6 (1H, m), 7.51 (1H, d), 7.14 (1H, s), 4.55 (2H, d), 3.20 (3H, s), 2.60 (3H, s) and 2.27 (3H, s).

EXAMPLE 19

3-(8-Fluoro-4-quinolinyl)-2,5-dimethyl-1H-indole-1-acetic acid, sodium salt a) 4-(2,5-Dimethyl-1H-indol-3-yl)-8-fluoroquinoline, hydrochloride The sub-title compound was prepared by the method of Example 15 step a, using 2,5-dimethylindole and 4-chloro-8-fluoroquinoline.

MS: ESI (+ve): 291 [M−Cl]⁺ b) Ethyl 3-(8-fluoro-4-quinolinyl)-2,5-dimethyl-1H-indole-1-acetate

The sub-title compound was prepared by the method of Example 15 step b, using the product of step a).

MS: ESI (+ve): 377 [M+H]⁺ c) 3-(8-Fluoro-4-quinolinyl)-2,5-dimethyl-1H-indole-1-acetic acid

The title compound was prepared by the method of Example 10 step c, using the product of step b).

MS: ESI (+ve): 349 [M−Na+2H]⁺ $^1$H NMR (DMSO-d6) δ 8.98 (1H, d), 7.63 (1H, d), 7.56 (1H, d), 7.46 (2H, d), 7.40 (1H, m), 6.98 (1H, d), 6.91 (1H, s), 4.45 (2H, t), 2.31 (3H, s), 2.23 (3H, s)

EXAMPLE 20

3-(2,8-Dimethyl-4-quinolinyl)-2,5-dimethyl-1H-indole-1-acetic acid, sodium salt a) 4-(2,5-Dimethyl-1H-indol-3-yl)-2,8-dimethylquinoline, hydrochloride The sub-title compound was prepared by the method of Example 15 step a, using 2,5-dimethylindole and 4-chloro-2,8-dimethylquinoline.

(MS: ESI (+ve): 301 [M−Cl]⁺ b) Ethyl 3-(2,8-Dimethyl-4-quinolinyl)-2,5-dimethyl-1H-indole-1-acetate

The sub-title compound was prepared by the method of Example 15 step b, using the product of step a).

MS: ESI (+ve): 387 [M+H]⁺, 100%.

c) 3-(2,8-Dimethyl-4-quinolinyl)-2,5-dimethyl-1H-indole-1-acetic acid, sodium salt The title compound was prepared by the method of Example 10 step c, using the product of step b).

MS: ESI (+ve): 359 [M−Na+2H]⁺ $^1$H NMR (DMSO-d6) δ 6.94 (1H, d), 6.81 (1H, d), 6.63 (1H, s), 6.54 (2H, m), 6.24 (1H, d), 6.21 (1H, d), 3.92 (2H, dd), 2.08 (3H, s), 2.05 (3H, s), 1.60 (3H, s), 1.54 (3H, s)

EXAMPLE 21

2,5-Dimethyl-3-[7-(trifluoromethyl)-4-(quinolinyl]-1H-indole-1-acetic acid, sodium salt a) 4-(2,5-Dimethyl-1H-indol-3-yl)-7-(trifluoromethyl)-quinoline, hydrochloride The sub-title compound was prepared by the method of Example 15 step a, using 2,5-dimethylindole and 4-chloro-7-trifluoromethylquinoline.

MS: ESI (+ve): 341 [M−Cl]⁺ b) Ethyl 2,5-dimethyl-3-[7-(trifluoromethyl)-4-quinolinyl]-1H-indole-1-acetate

The sub-title compound was prepared by the method of Example 15 step b, using the product of step a).

MS: ESI (+ve): 427 [M+H]⁺ c) 2,5-Dimethyl-3-[7-(trifluoromethyl)-4-quinolinyl]-1H-indole-1-acetic acid, sodium salt The title compound was prepared by the method of Example 10 step c, using the product of step b).

MS: ESI (+ve): 399 [M−Na+2H]⁺ $^1$H NMR (DMSO-d6) δ 9.09 (1H, d), 8.43 (1H, s), 8.02 (1H, d), 7.79 (1H, dd), 7.61 (1H, d), 7.27 (1H, d), 6.95 (1H, s), 6.94 (1H, d), 4.44 (2H, t), 2.31 (3H, s), 2.25 (3H, s)

EXAMPLE 22

3-(8-Bromo-2-methyl-4-quinolinyl)-2,5-dimethyl-1H-indole-1-acetic acid, sodium salt a) 8-Bromo-4-(2,5-dimethyl-1H-indol-3-yl)-2-methylquinoline, hydrochloride The sub-title compound was prepared by the method of Example 15 step a, using 2,5-dimethylindole and 8-bromo-4-chloro-2-methylquinoline.

MS: ESI (+ve): 365/7 [M−Cl]⁺, 100%.

b) Ethyl 3-(8-Bromo-2-methyl-4-quinolinyl)-2,5-dimethyl-1H-indole-1-acetate

The sub-title compound was prepared by the method of Example 15 step b, using the product of step a).

MS: ESI (+ve): 451/3 [M+H]⁺, 100%.

c) 3-(8-Bromo-2-methyl-4-quinolinyl)-2,5-dimethyl-1H-indole-1-acetic acid, sodium salt The title compound was prepared by the method of Example 10 step c, using the product of step b).

MS: ESI (+ve): 423/5 [M−Na+2H]⁺, 100%. $^1$H NMR (DMSO-d6) δ 8.08 (1H, d), 7.74 (1H, d), 7.41 (1H, s), 7.33 (1H, t), 7.25 (1H, d), 6.93-6.89 (2H, m), 4.45 (2H, dd), 2.77 (3H, s), 2.31 (3H, s), 2.23 (3H, s)

EXAMPLE 23

3-(8-Methoxy-2-methyl-4-quinolinyl)-2,5-dimethyl-1H-indole-1-acetic acid, sodium salt a) 4-(2,5-Dimethyl-1H-indol-3-yl)-8-methoxy-2-methylquinoline, hydrochloride The sub-title compound was prepared by the method of Example 15 step a), using 2,5-dimethylindole and 4-chloro-8-methoxy-2-methylquinoline.

MS: ESI (+ve): 303 [M−Cl]⁺, 100%.

b) Ethyl 3-(8-methoxy-2-methyl-4-quinolinyl)-2,5-dimethyl-1H-indole-1-acetate

The sub-title compound was prepared by the method of Example 15 step b), using the product of step a).

MS: ESI (+ve): 389 [M+H]⁺, 100%.

c) 3-(8-Methoxy-2-methyl-4-quinolinyl)-2,5-dimethyl-1H-indole-1-acetic acid, sodium salt The title compound was prepared by the method of Example 10 step c), using the product of step b).

MS: ESI (+ve): 361 [M−Na+2H]⁺, 100% ¹H NMR (DMSO-d6) δ 8.86 (1H, d), 7.46 (1H, m), 7.39 (1H, d), 7.33 (1H, dd), 7.24 (1H, d), 7.19 (1H, d), 6.92-6.88 (2H, m), 4.44 (2H, dd), 4.02 (3H, s), 2.30 (3H, s), 2.21 (3H, s)

EXAMPLE 24

3-(6,8-Dimethyl-4-quinolinyl)-2,5-dimethyl-1H-indole-1-acetic acid, sodium salt a) 4-(2,5-Dimethyl-1H-indol-3-yl)-6,8-dimethylquinoline hydrochloride The sub-title compound was prepared by the method of Example 15 step a) using 2,5-dimethylindole and 4-chloro-6,8-dimethylquinoline.

MS: ESI (+ve): 301 [M−Cl]⁺ b) Ethyl 3-(6,8-Dimethyl-4-quinolinyl)-2,5-dimethyl-1H-indole-1-acetate

The sub-title compound was prepared by the method of Example 15 step b), using the product of step a).

MS: ESI (+ve): 387 [M+H]⁺ c) 3-(6,8-Dimethyl-4-quinolinyl)-2,5-dimethyl-1H-indole-1-acetic acid, sodium salt The title compound was prepared by the method of Example 10 step c) using the product of step b).

MS: ESI (+ve): 359 [M−Na+2H]⁺ ¹H NMR (DMSO-d6) δ 8.86 (1H, d), 7.44 (2H, d), 7.37 (1H, d), 7.23 (1H, d), 6.92-6.88 (2H, m), 4.45 (2H, s), 2.77 (3H, s), 2.36 (3H, s), 2.30 (3H, s), 2.21 (3H, s)

EXAMPLE 25

3-(8-Chloro-4-quinolinyl)-2,5-dimethyl-1H-indole-1-acetic acids sodium salt a) 4-(2,5-Dimethyl-1H-indol-3-yl)-8-chloroquinoline, hydrochloride The sub-title compound was prepared by the method of Example 15 step a), using 2,5-dimethylindole and 4,8-dichloroquinoline.

MS: ESI (+ve): 307 [M−Cl]⁺ b) Ethyl 3-(8-chloro-4-quinolinyl)-2,5-dimethyl-1H-indole-1-acetate

The sub-title compound was prepared by the method of Example 15 step b), using the product of step a).

MS: ESI (+ve): 393 [M+H]⁺ c) 3-(8-Chloro-4-quinolinyl)-2,5-dimethyl-1H-indole-1-acetic acid, sodium salt

The title compound was prepared by the method of Example 10 step c) using the product of step b).

MS: ESI (+ve): 365 [M−Na+2H]⁺ ¹H NMR (DMSO-d6) δ 9.04 (1H, d), 7.96 (1H, dd), 7.78 (1H, dd), 7.55 (1H, d), 7.49 (1H, t), 7.26 (1H, d), 6.94-6.90 (2H, m), 4.45 (2H, dd), 2.31 (3H, s), 2.22 (3H, s)

EXAMPLE 26

3-(7-Chloro-4-quinolinyl)-2-methyl-5-nitro-1H-indole-1-acetic acid, sodium salt a) 7-Chloro-4-(2-methyl-5-nitro-1H-indol-3-yl)-quinoline, hydrochloride A mixture of 2-methyl-5-nitroindole (1.34 g) and 4,7-dichloroquinoline (1.53 g) in NMP (1 ml) and 4M HCl in dioxane (0.1 ml) was heated at 145° C. for 2 hours and at 160° C. for 4 hours. After cooling the mixture triturated with ether and the solid collected to give the sub-title compound (2.72 g) as a green solid.

MS: ESI (+ve): 338 [M−Cl]⁺ b) Ethyl 3-(7-chloro-4-quinolinyl)-2-methyl-5-nitro-1H-indole-1-acetate

A solution of the product from step a) (1.90 g), ethyl bromoacetate (0.68 ml) and caesium carbonate (3.3 g) in acetone (40 ml) was stirred for 24 hours, water was added and the mixture was extracted with ethyl acetate three times. The organic extracts were dried (MgSO₄), evaporated and purified by chromatography (silica, petrol-acetone as eluent) gave the sub-title compound (1.19 g).

MS: ESI (+ve): 424 [M+H]⁺ c) 3-(7-Chloro-4-quinolinyl)-2-methyl-5-nitro-1H-indole-1-acetic acid, sodium salt The title compound was prepared by the method of Example 10 step c) using the product of step b).

MS: ESI (+ve): 396 [M−Na+2H]⁺ ¹H NMR (DMSO-d6) δ 9.03 (1H, d), 8.20 (1H, d), 8.05-8.00 (2H, m), 7.75 (1H, d), 7.67-7.55 (3H, m), 4.64 (2H, s), 2.28 (3H, s)

EXAMPLE 27

5-chloro-3-(7-chloro-4-quinolinyl)-2-methyl-1H-indole-1-acetic acid a) Methyl 5-chloro-3-(7-chloro-4-quinolinyl)-2-methyl-1H-indole-1-acetate 5-Chloro-2-methylindole (0.16 g) and 4,8-dichloroquinoline (0.2 g) were suspended in NMP (0.5 ml) and heated in a microwave at 100W, 140° C. for 60 minutes. When reaction was complete THF (5 ml) was added followed by sodium hydride 60% dispersion in oil (0.12 g). After 30 mins a solution of methyl bromoacetate (0.2 ml) in THF (1 ml) was added and the mixture stirred at room temperature for 24 hours. Ethyl acetate and saturated brine solution were added, the aqueous phase was separated and extracted with ethyl acetate. The combined organic solution was evaporated to leave a residue which was purified by silica gel chromatography using dichloromethane/ethyl acetate (9:1) to provide the sub-title product as an oil. (120 mg).

MS: APCI (+ve): 399/401/403 [M+H]⁺ b) [5-chloro-3-(7-chloroquinolin-4-yl)-2-methyl-1H-indol-1-yl]acetic acid

A solution of lithium hydroxide monohydrate (0.26 g) in water (1 ml) was added to a solution of the product from step a) (** mg) in THF (4 ml) and the solution was stirred at room temperature for 16 hours. Ethyl acetate and saturated brine solution were added, the aqueous phase was separated and extracted with ethyl acetate. The organic solution was evaporated to leave a residue which was purified by Reverse Phase Preparative HPLC to give the product as a powder (34 mg).

MS: APCI (−ve): 383/385/387 [M−H]⁻ ¹H NMR (DMSO-d6) δ 9.0 (1H, d), 8.17 (1H, d), 7.69 (1H, d), 7.6 (2H, dd), 7.52 (1H, d), 7.19 (1H, dd), 7.12 (1H, d), 5.13 (2H, s), 4.45 (2H, q), 2.23 (3H, s)

EXAMPLE 28

5-chloro-2-methyl-3-(8-methyl-4-quinolinyl)-1H-indole-1-acetic acid a) 5-chloro-2-methyl-3-(8-methyl-4-quinolinyl)-1H-indole-1-acetic acid, methyl ester The sub-title product was prepared by the method of Example 27 step a), using 5-chloro-2-methylindole and 4-chloro-8-methylquinoline.

MS: APCI (+ve): 379/81 [M+H]$^+$ b) [5-chloro-2-methyl-3-(8-methylquinolin-4-yl)-1H-indol-1-yl]acetic acid The title compound was prepared by the method of Example 27 step b), using the product of step a).

MS: APCI (−ve): 363/65 [M−H]$^{31}$ $^1$H NMR (DMSO-d6) δ 8.98 (1H, d), 7.64 (1H, d), 7.59 (1H, d), 7.52-7.44 (2H, m), 7.42 (1H, t), 7.18 (1H, dd), 7.06 (1H, d), 5.14 (2H, s), 2.79 (3H, s), 2.23 (3H, s)

EXAMPLE 29

5-chloro-3-(6-methoxy-2-methyl-4-quinolinyl)-2-methyl-1H-indole-1-acetic acid a) 5-chloro-3-(6-methoxy-2-methyl-4-quinolinyl)-2-methyl-1H-indole-1-acetic acid, methyl ester The sub-title product was prepared by the method of Example 27 step a) using 5-chloro-2-methylindole and 4-chloro-6-methoxy-2-methylquinoline.

MS: APCI (+ve): 409/11 [M+H]$^+$ b) 5-chloro-3-(6-methoxy-2-methyl-4-quinolinyl)-2-methyl-1H-indole-1-acetic acid The title compound was prepared by the method of Example 27 step b), using the product of step a) to give the product as a powder.

MS: APCI (−ve): 393/95 [M−H]$^1$H NMR (DMSO-d6) δ 7.92 (1H, d), 7.61 (1H, d), 7.39 (1H, d), 7.36 (1H, d), 7.19 (1H, t), 7.18 (1H, d), 6.93 (1H, d), 5.14 (2H, q), 3.65 (3H, s), 2.67 (3H, s), 2.23 (3H, s)

EXAMPLE 30

5-Methoxy-2-methyl-3-(8-methyl-4-quinolinyl)-1H-indole-1-acetic acid, sodium salt a) 4-(5-Methoxy-2-methyl-1H-indol-3-yl)-8-methyl-quinoline A mixture of 5-methoxy-2-methylindole (346 mg) and 4-chloro-8-trifluoromethylquinoline (380 mg) in NMP (1 ml) and 4M HCl in dioxane (0.1 ml) was heated at 140° C. for 50 min. Aqueous sodium bicarbonate was added and the mixture was extracted with ethyl acetate. The organic extracts were dried (MgSO$_4$), evaporated and purified by chromatography (silica, petrol-acetone as eluent) to give the sub-title compound (465 mg).

MS: ESI (+ve): 303 [M+H]$^+$ b) Ethyl 5-methoxy-2-methyl-3-(8-methyl-4-quinolinyl)-1H-indole-1-acetate The sub-title compound was prepared by the method of Example 15 step b), using the product of step a).

MS: ESI (+ve): 389 [M+H]$^+$ c) 5-Methoxy-2-methyl-3-(8-methyl-4-quinolinyl)-1H-indole-1-acetic acid, sodium salt The title compound was prepared by the method of Example 10 step c) using the product of step b).

MS: ESI (+ve): 361 [Na+2H]$^+$ $^1$H NMR (DMSO-d6) δ 8.96 (1H, d), 7.70-7.57 (2H, m), 7.47-7.35 (2H, m), 7.27 (1H, d), 6.73 (1H, d), 6.60 (1H, d), 4.47 (2H, s), 3.60 (3H, s), 2.79 (3H, s), 2.21 (3H, s)

EXAMPLE 31

3-(7-chloro-4-quinolinyl)-5-fluoro-2-methyl-1H-indole-1-acetic acid a) 7-chloro-4-(5-fluoro-2-methyl-1H-indol-3-yl)-quinoline A solution of 5-fluoro-2-methylindole (149 mg) and 4,7-dichloroquinoline (198 mg) in NMP (2 ml) and 4M hydrogen chloride in dioxane (0.2 ml) was stirred at 140° C. overnight and then at 150° C. for 1 h. and evaporated. The residue was taken up in ethyl acetate, washed with brine (3×), dried (MgSO$_4$) and evaporated in vacuo. The residue was purified by silica chromatography using acetone/isohexane (2:8) as eluent to give the sub-title compound (250 mg).

b) 3-(7-chloro-4-quinolinyl)-5-fluoro-2-methyl-1H-indole-1-acetic acid

A stirred suspension of the product from step a) (250 mg) and caesium carbonate (525 mg) in acetone (20 ml) was treated with methyl bromoacetate (300 mg) and heated under reflux overnight. The mixture was evaporated. The residue was taken up in ethyl acetate, washed with water and evaporated in vacuo. The residue was taken up in THF (20 ml), treated with a solution of lithium hydroxide (58 mg) in water (5 ml), stirred overnight and concentrated to remove most of the THF. The solution was acidified with 1M hydrochloric acid and extracted with ethyl acetate. The dried (MgSO$_4$) extracts were evaporated to give a gum that was purified by reversed phase preparative HPLC gave the title compound (36 mg).

MS: APCI (+ve): 369 [M+H]$^+$ $^1$H NMR DMSO-d6) δ 8.99 (1H, d), 8.22 (1H, d), 7.83-7.46 (4H, m), 7.17-6.77 (2H, m), 5.19 (2H, s), 2.30 (3H, s)

EXAMPLE 32

5-fluoro-2-methyl-3-[8-(trifluoromethyl)-4-quinolinyl]-1H-indole-1-acetic acid a) 4-(5-fluoro-2-methyl-1H-indol-3-yl)-8-(trifluoromethyl)-quinoline The sub-title compound was prepared from 5-fluoro-2-methylindole and 4-chloro-8-trifluoromethylquinoline by the method of Example 31, step a).

b) 5-fluoro-2-methyl-3-[8-(trifluoromethyl)-4-quinolinyl]-1H-indole-1-acetic acid The title compound was prepared from the product of step a, by the method of Example 31, step b).

MS: APCI (−ve): 401 [M−H]$^-$ $^1$H NMR (DMSO-d6) δ 9.11 (1H, d), 8.23 (1H, d), 7.99 (1H, d), 7.75-7.56 (3H, m), 7.04 (1H, m), 6.89 (1H, m), 5.17 (2H, s), 2.25 (3H, s)

EXAMPLE 33

5-fluoro-2-methyl-3-(8-methyl-4-quinolinyl)-1H-indole-1-acetic acid a) 4-(5-fluoro-2-methyl-1H-indol-3-yl)-8-methyl-quinoline The sub-title compound was prepared from 5-fluoro-2-methylindole and 4-chloro-8-methylquinoline by the method of Example 31, step a).

b) 5-fluoro-2-methyl-3-(8-methyl-4-quinolinyl)-1H-indole-1-acetic acid

The title compound was prepared from the product of step a) by the method of Example 31, step b).

MS: APCI (+ve): 349 [M+H]+ 1H NMR (DMSO-d6) δ 8.96 (1H, d), 7.65-7.54 (2H, m), 7.49-7.33 (3H, m), 6.93 (1H, m), 6.80 (1H, m), 4.64 (2H, d), 2.79 (3H, s), 1.89 (3H, s)

EXAMPLE 34

2-methyl-3-(8-methyl-4-quinolinyl)-5-(trifluoromethyl)-1H-indole-1-acetic acid a) methyl-4-[2-methyl-5-(trifluoromethyl)-1H-indol-3-yl]-quinoline The sub-title compound was prepared from 2-methyl-5-(trifluoromethyl)-indole and 4-chloro-8-methylquinoline by the method of Example 31, step a).

b) 2-methyl-3-(8-methyl-4-quinolinyl)-5-(trifluoromethyl)-1H-indole-1-acetic acid The title compound was prepared from the product from step a) by the method of Example 31, step b).

MS: APCI (+ve): 397 [M+H]+ 1H NMR(DMSO-d6) δ 9.01 (1H, d), 7.71 (1H, d), 7.67-7.62 (1H, m), 7.55-7.48 (2H, m), 7.46-7.36 (3H, m), 4.98 (2H, s), 2.80 (3H, s), 2.25 (3H, s)

EXAMPLE 35

3-(1,2-benzisothiazol-3-yl)-2-methyl-5-(trifluoromethyl)-1H-indole-1-acetic acid a) 3-[2-methyl-5-(trifluoromethyl)-1H-indol-3-yl]-1,2-benzisothiazole The sub-title compound was prepared from 2-methyl-5-(trifluoromethyl)-indole 400 mg) and 3-chloro-1,2-benzisothiazole (338 mg) by the method of Example 31, step a) (400 mg)

b) 3-(1,2-benzisothiazol-3-yl)-2-methyl-5-(trifluoromethyl)-1H-indole-1-acetic acid The title compound was prepared from the product of step a, by the method of Example 31, step b).

MS: APCI (-ve): 389 [M-H]− 1H NMR (DMSO-d6) δ 8.31 (1H, d), 7.86 (1H, d), 7.75-7.62 (3H, m), 7.55-7.41 (2H, m), 4.92 (2H, s), 2.45 (3H, s)

EXAMPLE 36

3-(1,2-benzisothiazol-3-yl)-5-fluoro-2-methyl-1H-indole-1-acetic acid a) 3-(5-fluoro-2-methyl-1H-indol-3-yl)-1,2-benzisothiazole The title compound was prepared from 5-fluoro-2-methylindole and 3-chloro-1,2-benzisothiazole by the method of Example 31, step a).

b) 3-(1,2-benzisothiazol-3-yl)-5-fluoro-2-methyl-1H-indole-1-acetic acid

The title compound was prepared from the product of step a, by the method of Example 31, step b).

MS: APCI (-ve): 339 [M-H]− 1H NMR (DMSO-d6) δ 7.82 (1H, m), 7.57 (1H, m), 7.48-7.37 (1H, m), 7.26 (1H, m), 7.09-6.98 (2H, m), 6.65 (1H, d), 5.04 (2H, d), 2.41 (3H, s).

EXAMPLE 37

3-(1,2-benzisothiazol-3-yl)-5-chloro-2-methyl-1H-indol-1-acetic acid a) Methyl [3-(1,2-benzisothiazol-3-yl)-5-chloro-2-methyl-1H-indol-1-yl]acetate The sub-title product was prepared by the method of Example 27 step a) using 5-chloro-2-methylindole and 3-chloro-1,2-benzisothiazole.

MS: APCI (+ve): 371/3 [M+H]+ b) 3-(1,2-benzisothiazol-3-yl)-5-chloro-2-methyl-1H-indol-1-acetic acid

The title compound was prepared by the method of Example 27 step b) using the product of step a).

MS: APCI (-ve): 355/57 [M-H]− 1H NMR (DMSO-d6) δ 8.28 (1H, d), 7.87 (1H, d), 7.66 (1H, t), 7.51 (1H, t), 7.44 (1H, d), 7.34 (1H, s), 7.11 (1H, d), 4.59 (2H, s), 2.32 (3H, s)

EXAMPLE 38

3-(1,2-benzisothiazol-3-yl)-4-methyl-1H-indole-1-acetic acid a) 3-(4-methyl-1H-indol-3-yl)-1,2-benzisothiazole The sub-title compound was prepared by the method of Example 16 step a) from 4 dimethyl indole and 3-chlorobenzisothiazole.

ES (+ve): 265 [M+H]+ b) 3-(1,2-benzisothiazol-3-yl)-4-methyl-1H-indole-1-acetic acid, ethyl ester

The sub-title compound was prepared by the method of Example 10 step b) using the product of step a).

c) 3-(1,2-benzisothiazol-3-yl)-4-methyl-1H-indole-1-acetic acid

The title compound was prepared by the method of Example 10 step c) using the product of step b).

1H NMR (DMSO-d6) δ 8.25 (1H, d), 7.69 (1H, d), 7.7 (1H, s), 7.61 (1H, t), 7.53 (1H, t), 7.26 (1H, d), 7.11 (1H, t), 6.83 (1H, d), 4.74 (2H, s), 2.0 (3H, s).

EXAMPLE 39

3-(1,2-benzisothiazol-3-yl)-2,4-dimethyl-1H-indole-1-acetic acid a) 3-(2.4-dimethyl-1H-indol-3-yl)-1,2-benzisothiazole The sub-title compound was prepared by the method of Example 16 step a) from 2,4 dimethyl indole and 3-chlorobenzisothiazole.

ES (+ve): 265 [M+H]+ b) 3-(1,2-benzisothiazol-3-yl)-2,4-dimethyl-1H-indole-1-acetic acid, ethyl ester The sub-title compound was prepared by the method of Example 10 step b) using the product of step a).

ES (+ve): 364 [M+H]+ c) 3-(1,2-benzisothiazol-3-yl)-2,4-dimethyl-1H-indole-1-acetic acid

The title compound was prepared by the method of Example 10 step c) using the product of step b).

1H NMR (DMSO-d6) δ 8.25 (1H, d), 7.62 (2H, m), 7.43 (1H, t), 7.2 (1H, d), 6.97 (1H, t), 6.7 (1H, d), 4.46 (2H, s), 2.14 (3H, s), 1.86 (3H, s).

EXAMPLE 40

3-(8-nitroquinolin-4-yl)-2,5-dimethyl-1H-indole-1-acetic acid a) 8-Nitro-(2,5-dimethyl-1H-indol-3-yl)quinoline 2,5-Dimethylindole (300 mg) and 8-nitro-4-chloroquinoline (430 mg) were suspended in NMP (10 ml) containing 4M HCl in dioxane (2 drops) and maintained under a nitrogen atmosphere. The reaction was heated to 120° C. with stirring for 8 hours. When cooled, the mixture was basified with saturated sodium hydrogen carbonate solution and extracted into ethyl acetate, dried (MgSO$_4$) and evaporated under reduced pressure to give an oil. The oil was purified by flash column chromatography using 2:1 isohexane/ethyl acetate as eluent to give the sub-title compound (560 mg).

MS: ESI (+ve): 318 [M+H]$^+$ b) 3-(8-nitroquinolin-4-yl)-2,5-dimethyl-1H-indole-1-acetic acid, ethyl ester The product of Example 40 step a) (0.56 g) and caesium carbonate (0.686 g) were suspended in dry acetonitrile (20 ml) followed by addition of ethyl bromoacetate (0.235 ml) and maintained under a nitrogen atmosphere. The reaction was heated to reflux for 6 hours. The solvents were evaporated under reduced pressure. The residue was subjected to flash column chromatography using 2:1 isohexane/ethyl acetate as eluent to give the sub-title compound (50 mg).

MS: ESI (+ve): 404 [M+H]$^+$ c) 3-(8-nitroquinolin-4-yl)-2,5-dimethyl-1H-indole-1-acetic acid The product of Example 40 step b) (0.50 g) was suspended in THF (10 ml) and to it added 1M sodium hydroxide (1.24 ml) for the mixture to be stirred overnight at room temperature to complete the reaction. The solution was evaporated to dryness and purified by Reverse Phase Preparative HPLC to give the title compound as a yellow solid (0.31 g).

MS: ESI (+ve): 376 [M+H]$^+$ $^1$H NMR (DMSO-d6) δ 9.05-9.03 (1H, d), 8.25-8.23 (1H, d), 8.03-8.00 (1H, d), 7.69-7.63 (2H, m), 7.29 (1H, d), 6.93 (2H, dd), 4.65-4.53 (2H, q), 2.29 (3H, s) 2.24 (3H, s)

EXAMPLE 41

3-(8-cyano-4-quinolinyl)-2,5-dimethyl-1H-indole-1-acetic acid a) 8-Cyano-(2,5-dimethyl-1H-indol-3-yl)quinoline The sub-title compound was prepared by the method of Example 40 step a, using 2,5-dimethyl indole and 8-cyano-4-chloroquinoline and 1 molar equivalent of 4M HCl in dioxane.

MS: ESI (+ve): 298 [M+H]$^+$ b) 3-(8-cyano-4-quinolinyl)-2,5-dimethyl-1H-indole-1-acetic acid, ethyl ester The sub-title compound was prepared by the method of Example 40 step b, using the product of step a.

MS: ESI (+ve): 384 [M+H]$^+$ c) 3-(8-cyano-4-quinolinyl)-2,5-dimethyl-1H-indole-1-acetic acid The title compound was prepared by the method of Example 40 step c, using the product of step b.

MS: ESI (+ve): 356 [M–H]$^-$ $^1$H NMR (DMSO-d6) δ 9.10-9.09 (1H, d), 8.38-8.35 (1H, d), 8.12-8.09 (1H, d), 7.69-7.62 (2H, m), 7.27-7.25 (1H, d), 6.95-6.92 (2H, dd), 4.49-4.37 (2H, q), 2.29 (3H, s), 2.21 (3H, s)

EXAMPLE 42

2,5-dimethyl-3-[8-(methylsulfonyl)-4-quinolinyl]-1H-indole-1-acetic acid a) 8-methanesulphonyl-(2,5-dimethyl-1H-indol-3-yl)quinoline The sub-title compound was prepared by the method of Example 40 step a, using 2,5-dimethyl indole and 8-methanesulphonyl-4-chloroquinoline.

MS: ESI (+ve): 351 [M+H]

b) 2,5-dimethyl-3-[8-(methylsulfonyl)-4-quinolinyl]-1H-indole-1-acetic acid, ethyl ester The sub-title compound was prepared by the method of Example 40 step b, using the product of step a.

MS: ESI (+ve): 437 [M+H]$^+$ c) 2,5-dimethyl-3-[8-(methylsulfonyl)-4-quinolinyl]-1H-indole-1-acetic acid The title compound was prepared by the method of Example 40 step c, using the product of step b.

MS: ESI (+ve): 407 [M+H]$^+$ $^1$H NMR (DMSO-d6) δ 9.13-9.12 (1H, d), 8.43-8.41 (1H, d), 8.14-8.11 (1H, d), 7.74-7.70 (1H, m), 7.64-7.63 (1H, d), 7.31-7.29 (1H, d), 6.95-6.94 (2H, dd), 4.63-4.54 (2H, q), 3.67 (3H, s), 2.28 (3H, s), 2.23 (3H, s)

EXAMPLE 43

2,5-dimethyl-3-(1,5-naphthyridin-4-yl)-1H-indole-1-acetic acid a) 4-(2,5-dimethyl-1H-indol-3-yl)-1,5-naphthyridine The sub-title compound was prepared by the method of Example 40 step a), using 2,5-dimethyl indole and 8-methanesulphonyl-4-chloroquinoline.

MS: ESI (+ve): 274 [M+H]$^+$ b) 2,5-dimethyl-3-(1,5-naphthyridin-4-yl)-1H-indole-1-acetic acid, ethyl ester The sub-title compound was prepared by the method of Example 40 step b), using the product of step a).

MS: ESI (+ve): 360 [M+H]$^+$ c) 2,5-dimethyl-3-(1,5-naphthyridin-4-yl)-1H-indole-1-acetic acid The title compound was prepared by the method of Example 40 step c), using the product of step b).

MS: ESI (+ve): 332 [M+]$^+$ $^1$H NMR (DMSO-d6) δ 9.00-8.99 (1H, d), 8.93-8.91 (1H, m), 8.46-8.43 (1H, dd), 7.79-7.72 (2H, m), 7.23-7.20 (1H, d) 7.09 (1H, m), 6.90-6.87 (1H, dd), 4.48 (2H, s), 2.30 (3H, s), 2.21 (3H, s)

EXAMPLE 44

3-[8-(difluoromethoxy)-4-quinolinyl]-2,5-dimethyl-1H-indole-1-acetic acid a) 5-(methoxymethylene)-2,2-dimethyl-1,3-dioxane-4,6-dione 2,2-Dimethyl-1,3-dioxane-4,6-dione (100 g) was heated in trimethylorthoformate (500 ml) at 100° C. for 2 h. The solution was evaporated under reduced pressure to give an oil. The oil was triturated with 1:1 isohexane/diethyl ether (400 ml) and the solid was filtrated and dried in vacuo to give the sub-title compound (99.8 g).

$^1$H NMR (CDCl$_3$) δ 8.15 (1H, s), 4.28 (3H, s), 1.77-1.71 (6H, s).

b) 8-(difluoromethoxy)-4-quinolinol 2-difluoromethoxyaniline (7.63 g) and the product from step a) were stirred in acetonitrile (100 ml) overnight. The solvent was removed by evaporation and the solid triturated with 4:1 isohexane/diethyl ether (200 ml) before filtering to give a light green solid. The solid was added portionwise to refluxing diphenylether (120 ml) and continued heating for a further 10 minutes before cooling. The solution was poured into isohexane (600 ml) and the solid filtered off to give the title compound (12.0 g).

$^1$H NMR (DMSO-d6) δ 11.54 (1H, bs), 7.96-7.93 (1H, d) 7.84-7.82 (1H, m), 7.54-7.52 (1H, d), 7.42-7.35 (1H, m), 7.16-6.99 (1H, m), 6.11-6.08 (1H, d).

c) 8-(difluoromethoxy)-4-chloroquinoline

The product from step b) was heated to reflux in phosphorus oxychloride (80 ml) for 1 hour. The reagent was evaporated under reduced pressure to give an oil which was carefully poured into a mixture of ice/880 ammonia solution (400 ml) and stirred for 30 minutes. The solid was filtered off and dried in vacuo to give the sub-title compound (6.80 g).

MS: ESI (+ve): 230 [M+H]+ $^1$H NMR (DMSO-d6) δ 8.92-8.91 (1H, d) 8.13-8.11 (1H, d), 7.91-7.89 (1H, d), 7.81-7.70 (1H, t), 7.69-7.65 (1H, d), 7.65-7.27 (1H, bt)

d) 8-(difluoromethoxy)-(2,5-dimethyl-1H-indol-3-yl)quinoline

The sub-title compound was prepared by the method of Example 40 step a), using 2,5-dimethyl indole and 8-difluoromethoxy-4-chloroquinoline.

MS: ESI (+ve): 339 [M+H]

e) 3-[8-(difluoromethoxy)-4-quinolinyl]-2,5-dimethyl-1H-indole-1-acetic acid, ethyl ester The sub-title compound was prepared by the method of Example 40 step b), using the product of step d).

MS: ESI (+ve): 425 [M+H]

f) 3-[8-(difluoromethoxy)-4-quinolinyl]-2,5-dimethyl-1H-indole-1-acetic acid

The title compound was prepared by the method of Example 40 step c) using the product of step e).

MS: ESI (+ve): 397 [M+H]+ $^1$H NMR (DMSO-d6) δ 9.00-8.99 (1H, d), 7.69-7.66 (1H, m), 7.57-7.49 (4H, m) 7.32-7.30 (1H, d), 6.95-6.93 (1H, dd), 4.72-4.63 (2H, q), 2.28 (3H, s), 2.21 (3H, s).

EXAMPLE 45

5-Amino-3-(7-chloro-4-quinolinyl)-2-methyl-1H-indole-1-acetic acid a) Ethyl 5-amino-3-(7-chloro-4-quinolinyl)-2-methyl-1H-indole-1-acetate A suspension of the product from Example 26, step b) (1.60 g) and 5% platinum on carbon 910 mg) in ethanol was stirred under 2 atmospheres of hydrogen for 16 h. The mixture was filtered, evaporated and purified by silica chromatography (petrol-acetone as eluent) to give the sub-title compound (1.17 g).

MS: ESI (+ve): 435 [M+H]+ b) 5-Amino-3-(7-chloro-4-quinolinyl)-2-methyl-1H-indole-1-acetic acid

The sub-title compound was prepared by the method of Example 15 step c) using the product of step b).

MS: ESI (+ve): 366 [M+H]+, 100%. $^1$H NMR (DMSO-d6) δ 8.95 (1H, d), 8.12 (1H, d), 7.82 (1H, d), 7.56 (1H, dd), 7.44 (1H, d), 7.13 (1H, d), 6.50 (1H, dd), 6.34 (1H, d), 4.72 (2H, s), 2.19 (2H, s), 1.91 (3H, s)

EXAMPLE 46

3-(7-Chloro-4-quinolinyl)-2-methyl-5-[(methylsulfonyl)amino]-1H-indole-1-acetic acid a) Ethyl 3-(7-chloro-4-quinolinyl)-2-methyl-5-[(methylsulfonyl)amino]-1H-indole-1-acetate Methane sulfonyl chloride (70 μl) was added to a solution of the product from Example 46 step a) and triethylamine (0.13 ml) in dichloromethane (3 ml) at 0° C. and stirred at 20° C. for 1 h. Water was added and the mixture was extracted with dichloromethane. The organic extracts were dried (MgSO$_4$), evaporated and purified by silica chromatography (petrol-acetone) to give the sub-title compound (238 mg).

MS: ESI (+ve): 472 [M+H]+, 100%.

b) 3-(7-Chloro-4-quinolinyl)-2-methyl-5-[(methylsulfonyl)amino]-1H-indole-1-acetic acid The title compound was prepared by the method of Example 15 step c), using the product of step a). M.p. 195-8° C.

MS: ESI (+ve): 444 [M+H]+ $^1$H NMR (DMSO-d6) δ 13.19 (1H, s), 9.24 (1H, s), 9.01 (1H, d), 8.17 (1H, d), 7.75 (1H, d), 7.61-7.49 (3H, m), 7.10 (1H, dd), 7.02 (1H, d), 5.13 (2H, s), 2.82 (3H, s), 2.26 (3H, s)

EXAMPLE 47

5-(Acetylamino)-3-(7-chloro-4-quinolinyl)-2-methyl-1H-indole-1-acetic acid a) Ethyl 5-(Acetylamino)-3-(7-chloro-4-quinolinyl)-2-methyl-1H-indole-1-acetate Acetyl chloride (60 μl) was added to a solution of the product from Example 46 step a) and triethylamine (0.13 ml) in dichloromethane (3 ml) at 0° C. and stirred at 20° C. for 1 hour. Water was added and the mixture was extracted with dichloromethane. The organic extracts were dried (MgSO$_4$), evaporated and purified by chromatography (silica, ethyl acetate as eluent) to give the sub-title compound (290 mg). M.p. 281-4° C.

MS: ESI (+ve): 436 [M+H]+ b) 5-(Acetylamino)-3-(7-chloro-4-quinolinyl)-2-methyl-1H-indole-1-acetic acid

The title compound was prepared by the method of Example 15 step c), using the product of step a).

MS: ESI (+ve): 408 [M+H]+ $^1$H NMR (DMSO-d6) δ 13.15 (1H, s), 9.72 (1H, s), 9.00 (1H, d), 8.17 (1H, d), 7.75 (1H, d), 7.59 (1H, dd), 7.52-7.36 (4H, m), 5.10 (2H, s), 2.25 (3H, s), 1.95 (3H, s)

EXAMPLE 48

3-(1,2-Benzisothiazol-3-yl)-7-chloro-5-fluoro-2,4-dimethyl-1H-indol-1-yl]acetic acid a) 7-Chloro-5-fluoro-2,4-dimethyl-3-methylthio-1H-indole A stirred solution of 2-chloro-4-fluoro-5-methylaniline (1.655 g) in methylene chloride (100 ml) under nitrogen was treated at −65° C. with a solution of $^t$butylhypochlorite (1.126 g) in methylene chloride (5 ml), stirred at −65° C. for 10 min, treated at −65° C. with a solution of methylthioacetone (1.080 g) in methylene chloride (5 ml) stirred at −65° C. for 1 hour, treated at −65° C. with triethylamine (1.05 g) and allowed to reach ambient temperature. The solution was washed, dried (MgSO$_4$) and evaporated. The residue was purified by silica chromatography using 25% acetone in isohexane as eluent to give the sub-title compound (1.704 g).

MS: APCI (−ve): 242 [M−H]− $^1$H NMR (DMSO-d6) δ 11.67 (1H, s), 7.07 (1H, d), 2.71 (3H, d), 2.48 (3H, s), 2.19 (3H, s).

b) 7-Chloro-5-fluoro-2,4-dimethyl-1H-indole

A solution of the product from part a) (1.134 g) and thiosalicylic acid (1.435 g) in trifluoroacetic acid (50 ml) was stirred at 60° C. for 2 h and evaporated. The residue was taken up in methylene chloride, washed with 1M aqueous sodium hydroxide solution followed by water, dried (MgSO$_4$) and evaporated. The residue was purified by silica chromatography using 10% ethyl acetate in isohexane as eluent to give the sub-title compound (817 mg).

MS: ESI: MW197, BP 196 $^1$H NMR (DMSO-d6) δ 11.25 (1H, s), 6.97 (1H, d), 6.28 (1H, q), 2.40 (3H, d), 2.30 (3H, d)

c) 3-(1,2-Benzisothiazol-3-yl)-7-chloro-5-fluoro-2,4-dimethyl-1H-indole

A solution of the product from step b) (200 mg) and 3-chloro-1,2-benzisothiazole (171 mg) in NMP (2 ml) and 4M hydrogen chloride in dioxane (0.2 ml) was stirred at 140° C. overnight and then at 150° C. for 1 hour. and evaporated. The residue was taken up in ethyl acetate, washed with brine (3×), dried (MgSO$_4$) and evaporated. The residue was purified by silica chromatography using 20% acetone in isohexane as eluent to give the title compound (219 mg).

MS: APCI (−ve): 331 [M+H]$^+$ $^1$H NMR (DMSO-d6) δ 8.33 (1H, s), 8.01 (1H, d), 7.66 (1H, d), 7.56 (1H, t), 7.39 (1H, t), 6.99 (1H, d), 2.34 (3H, s), 1.79 (3H, d).

d) 3-(1,2-Benzisothiazol-3-yl)-7-chloro-5-fluoro-2,4-dimethyl-1H-indol-1-yl]acetic acid A stirred suspension of the product from step c) (205 mg) and caesium carbonate (493 mg) in acetone (20 ml) was treated with methyl bromoacetate (217 mg) and heated under reflux overnight. The mixture was evaporated. The residue was taken up in ethyl acetate, washed and evaporated. The residue was taken up in THF (20 ml), treated with a solution of lithium hydroxide (26 mg) in water (5 ml), stirred overnight, treated with more lithium hydroxide (78 mg), stirred for 2 hours and concentrated to remove most of the THF. The solution was acidified with 1M hydrochloric acid and extracted with ethyl acetate. The washed and dried (MgSO$_4$) extracts were evaporated to give a gum that was purified by reversed phase preparative HPLC on 19×50 mm Xterra C8 column using 5 to 90% acetonitrile in 0.2% aqueous 0.880 ammonia over 7 mins at 20 ml/min. The clean eluents were freeze dried to give the title compound (168 mg).

MS: APCI (−ve): 387 [M+H]$^+$ $^1$H NMR (DMSO-d6) δ 8.28 (1H, d), 7.64 (1H, ddd), 7.58 (1H, d), 7.47 (1H, ddd), 7.04 (1H, d), 4.97 (2H, dd), 2.08 (3H, s), 1.65 (3H, d).

EXAMPLE 49

3-(1,2-Benzisothiazol-3-yl)-5-fluoro-2,4-dimethyl-1H-indol-1-yl]acetic acid a) 5-Fluoro-2,4-dimethyl-1H-indole A stirred suspension of 10% palladium on carbon (200 mg) in ethanol (50 ml) was treated with a solution of ammonium formate (2.3 g) in water (2 ml), stirred for 1 min, treated with a solution the product from Example 48, part b (721 mg) in ethanol (10 ml), stirred for 2 days, treated with more 10% palladium on carbon (500 mg), stirred at 40° C. for 2 hours and filtered. The solids were washed with ethanol and the combined filtrates were evaporated. The residue was taken in ether, washed, dried (MgSO$_4$) and evaporated to give the sub-title compound.

MS: ESI: 163[M+H]$^+$ BP 162° C. $^1$H NMR DMSO-d6) δ 7.82 (1H, s), 7.04-7.01 (1H, m), 6.82 (1H, dd), 6.21-6.21 (1H, m), 2.45 (3H, s), 2.40-2.40 (3H, m).

b) 3-(1,2-Benzisothiazol-3-yl)-5-fluoro-2,4-dimethyl-1H-indole

The sub-title compound was prepared from the product of step a) (165 mg) and 3-chloro-1,2-benzisothiazole (171 mg) by the method of Example 48, step c (93 mg).

MS: APCI (−ve): 297 [M+H]$^+$ $^1$H NMR (DMSO-d6) δ (1H, s), 8.00 (1H, d), 7.69-7.66 (1H, m), 7.57-7.51 (1H, m), 7.39-7.34 (1H, m), 7.03-6.99 (1H, m), 6.85 (1H, t), 2.13 (3H, s), 1.83 (3H, d).

c) 3-(1,2-Benzisothiazol-3-yl)-5-fluoro-2,4-dimethyl-1H-indol-1-yl]acetic acid

The title compound was prepared from the product from step b, by the method of Example 48, step d.

MS: APCI (−ve): 353 [M−H]$^-$ $^1$H NMR DMSO-d6) δ 8.26 (1H, d), 7.64-7.59 (2H, m), 7.45 (1H, ddd), 7.28-7.25 (1H, m), 6.94-6.89 (1H, m), 4.70 (2H, s), 2.13 (3H, s), 1.74 (3H, d)

EXAMPLE 50

3-(7-Chloro-4-quinolin-4-yl)-5-fluoro-2,4-dimethyl-1H-indol-1-yl]acetic acid a) 3-(7-Chloro-4-quinolin-4-yl)-5-fluoro-2,4-dimethyl-1H-indole The sub-title compound was prepared from the product of Example 49, step a) and 4,7-dichloroquinoline by the method of Example 48, step c).

MS: APCI (−ve): 331 [M+H]$^+$ $^1$H NMR (CDCl$_3$) δ 8.96 (1H, d), 8.46 (1H, s), 8.18 (1H, d), 7.61 (1H, d), 7.40-7.36 (2H, m), 7.19-7.15 (1H, m), 6.93 (1H, t), 2.18-2.18 (3H, m), 1.71 (3H, d)

b) 3-(7-Chloro-4-quinolin-4-yl)-5-fluoro-2,4-dimethyl-1H-indol-1-yl]acetic acid

The title compound was prepared from the product from step a), by the method of Example 48, step d). Purification by reversed phase preparative HPLC to give the title compound.

MS: APCI (−ve): 381 [M−M]$^-$ $^1$H NMR (DMSO-d6) δ 8.99 (1H, d), 8.16-8.15 (1H, m), 7.56-7.55 (2H, m), 7.51 (1H, d), 7.37-7.33 (1H, m), 6.95 (1H, t), 4.94 (2H, s), 2.06 (3H, s), 1.61 (3H, d).

EXAMPLE 51

5-Chloro-2-methyl-3-(8-(quinolinyl)-1H-indole-1-acetic acid a) 5-chloro-3-iodo-2-methyl-1H-indole-1-acetic acid A solution of iodine (14 g) was added dropwise over 10 mins to a solution of the 5-chloro-2-methyl indole (8.3 g) and 4-chlorothiophenol (8 g) in ethanol (250 ml) and stirred for 1 hour. The mixture was concentrated in vacuo and the residue was treated with diethyl ether to give the sub-title compound as an off white solid (9.9 g)

MS: APCI (+ve): 291 [M+H]$^+$ b) 5-chloro-3-iodo-2-methyl-1H-indole-1-acetic acid, ethyl ester The product of step a) (9.9 g) was dissolved in DMF (60 ml), treated with sodium hydride (1.65 g) and stirred for 30 min. Ethyl bromoacetate (6.9 ml) was added and the reaction mixture stirred for a further 30 min. The reaction was quenched with dilute acetic acid (300 ml), extacted EtOAc (×3), then washed water, brine, dried (MgSO$_4$) and concentrated in vacuo. The residue was purified by silica chromatography eluting with EtOAc/hexane (25:75 v/v) to afford the sub-title compound (8.5 g).

MS: APCI (+ve): 379 [M+H]$^+$ c) 5-Chloro-2-methyl-3-(8-quinolinyl)-1H-indole-1-acetic acid The product of part b (250 mg), 7-quinoline boronic acid (114 mg), 2M sodium bicarbonate (0.7 ml), toluene, ethanol, tetrakis palladium triphenyl phosphine (0) and lithium chloride were heated at reflux for 2 hours. The reaction mixture was concentrated in vacuo, purified using amine resin and then by reverse phase preparative HPLC to give the title compound as a white solid.

$^1$H NMR (DMSO-d6) δ 8.81 (1H, s), 8.43 (1H, d), 8.02-7.97 (1H, m), 7.78-7.7 (1H, m), 7.39 (1H, d), 7.04 (2H, m), 4.67 (2H, s), 2.2 (3H, s).

EXAMPLE 52

5-chloro-2-methyl-[3,5'-bi-1H-indole]-1-acetic acid a) 5-chloro-2-methyl-[3,5'-bi-1H-indole]-1-acetic acid, ethyl ester The product of Example 51 part b (200 mg), 5-indole boronic acid (100 mg), potassium carbonate (0.73 g), acetone (6 ml), water (3 ml), palladium acetate (12 mg) and tri(o-tolyl) phosphine (30 mg) were heated at 90° C. for 4 hours. The reaction mixture was concentrated in vacuo, purified by silica chromatography eluting with hexane:EtOAc (7:3) to give the sub-title compound (140 mg).

MS (APCI$^+$) 369 [M+H]$^+$ b) 5-chloro-2-methyl-[3,5'-bi-1H-indole]-1-acetic acid The product from part a) (121 mg) was treated with NaOH (0.3 ml), THF (3 ml) and ethanol (1 ml), stirred for 1 h, concentrated in vacuo. The residue was dissolved in ethyl acetate and water. The aqueous phase was concentrated in vacuo and further purified by preparative reverse phase chromatography to give the title compound as a white solid (47 mg).

$^1$H NMR (DMSO-d6) δ 7.59-7.23(5H, m), 7.18 (1H, d), 7.0 (1H, d), 6.47 (1H, s), 4.52 (2H, s), 7.04 (2H, m), 2.39 (3H, s).

EXAMPLE 53

3-benzo[b]thien-3-yl-5-chloro-2-methyl-1H-indole-1-acetic acid a) 3-benzo[b]thien-3-yl-5-chloro-2-methyl-1H-indole-1-acetic acid, ethyl ester The product of Example 51 part b (600 mg), benzothiaphene-3-boronic acid (420 mg), potassium carbonate (35 mg), acetone (18 ml), water (9 ml) and palladium acetate tri(o-tolyl) phoshine (97 mg) were heated at 90° C. for 2 h. The reaction mixture was concentrated in vacuo, purified (SiO$_2$ chromatography), eluting with hexane:ether (8:2 v/v) to give the sub-title compound (270 mg), then hexane:methanol:acetic acid (1:1:0.5 v/v) to give the crude title compound. This was further purified by preparative reverse phase HPLC to give the title compound (30 mg).

b) 3-benzo[b]thien-3-yl-5-chloro-2-methyl-1H-indole-1-acetic acid

The sub-title compound was prepared by the method of Example 52 step b) using the product of step a).

$^1$H NMR (DMSO-d6) δ 8.07 (1H, dd), 7.63 (1H, s), 7.53-7.37 (4H, m), 7.18 (1H, d), 7.05 (1H, dd), 4.63 (2H, s) and 2.28 (3H, s).

EXAMPLE 54

2,5-Dimethyl-3-thieno[2,3-d]pyrimidin-4-yl 1H-indole-1-acetic acid a) 4-(2,5-Dimethyl-1H-indol-3-yl)-thieno[2,3-d]pyrimidine, hydrochloride The sub-title compound was prepared by the method of Example 15 step a) using 2,5-dimethylindole and 4-chlorothieno[2,3-d]pyrimidine.

MS: ESI (+ve): 280 [M–Cl]$^+$ b) Ethyl 2,5-dimethyl-3-thieno[2,3-d]pyrimidin-4-yl 1H-indole-1-acetate The sub-title compound was prepared by the method of Example 15 step b) using the product of step a).

MS: ESI (+ve): 366 [M+H]$^+$, 100%.

c) 2,5-Dimethyl-3-thieno[2,3-d]pyrimidin-4-yl 1H-indole-1-acetic acid

The title compound was prepared by the method of Example 15 step c) using the product of step b).

MS: ESI (+ve): 338 [M+H]$^+$, 100%. $^1$H NMR (DMSO-d6) δ 9.09 (1H, s), 9.09 (1H, s), 7.90 (1H, d), 7.35-7.26 (3H, m), 4.70 (2H, s), 2.45 (3H, s), 2.34 (3H, s)

EXAMPLE 55

5-Chloro-3-(7-chloro-4-quinolinyl)-2-(hydroxymethyl)-1H-indole-1-acetic acid 1-Bromo-2,5-pyrrolidinedione (0.26 g) was added to a solution of the product from Example 27 step b) (0.5 g) in DMF (5 ml) and the solution stirred at room temperature for 20 mins. Water (5 ml) was added and the mixture stirred for a further 30 mins. The reaction was diluted with further water (50 ml), extracted with ethyl acetate, dried (MgSO$_4$) and filtered. The filtrate was evaporated in vacuo and the residue purified by reverse phase HPLC. After evaporation in vacuo the oily residue was treated with ether to give a solid. Filtered off and dried to yield the title compound as a white solid (48 mg). MS (APCI) 399 [M–H]$^-$ $^1$H NMR (DMSO-d6) δ 9.01 (1H, d), 8.17 (1H, s), 7.79 (1H, d), 7.59 (3H, m), 7.23 (1H, d), 7.13 (1H, s), 5.01 (2H, s), 4.44 (2H, dd)

EXAMPLE 56

5-Chloro-3-(7-chloro-4-quinolinyl)-2-(methoxymethyl)-1H-indole-1-acetic acid 1-Bromo-2,5-pyrrolidinedione (0.26 g) was added to a solution of the product from Example 27 step b) (0.5 g) in DMF (5 ml) and methanol (2 ml), and the solution stirred for 1 h. The solvents were evaporated in vacuo and the residue purified by reverse phase HPLC. After evaporation in vacuo the oily residue was treated with ether to give a solid, which was filtered and dried to yield the title compound as a white solid (48 mg).

MS (APCI–) 413 [M–H]$^-$ $^1$H NMR (DMSO-d6) δ 9.02 (1H, d), 8.18 (1H, s), 7.71 (1H, d), 7.65 (1H, d), 7.61 (1H, d), 7.52 (1H, d), 7.27 (1H, d), 7.15 (1H, s), 5.12 (2H, s), 4.42 (2H, dd), 3.08 (3H, s)

EXAMPLE 57

2-[(Acetyloxy)methyl]-5-chloro-3-(7-chloro-4-quinolinyl)-1H-indole-1-acetic acid 1-Bromo-2,5-pyrrolidinedione (50 mg) was added to a solution of the product from Example 27 step b) (0.1 g) in 1,2-dichloroethane (5 ml) and acetic acid (2 ml), and the solution stirred for 1 hour. The solvents were evaporated in vacuo and the residue purified by reverse phase HPLC. After evaporation in vacuo the oily residue was treated with ether to give a solid, which was filtered and dried to yield the title compound as a white solid (40 Mg).

MS (APCI–) 441 [M–H]$^-$ $^1$H NMR (DMSO-d6) δ 9.03 (1H, d), 8.18 (1H, s), 7.71 (1H, d), 7.64 (1H, s), 7.62 (1H, s), 7.55 (1H, d), 7.30 (1H, d), 7.17 (1H, s), 5.20 (2H, s), 5.10 (2H, dd), 1.91 (3H, s)

EXAMPLE 58

5-Chloro-3-(7-chloro-4-quinolinyl)-2-[(methylamino)methyl]-1H-indole-1-acetic acid 1-Bromo-2,5-pyrrolidinedione (125 mg) was added to a solution of the product from Example 27 step b) (250 mg) in NW (0.5 ml) and dichloromethane (5 ml), and the solution stirred for 30 min. 2M methylamine/THF (3.25 ml) was then added and the solution stirred for 1 hour. The mixture was diluted with dichloromethane (20 ml), washed with saturated aqueous sodium bicarbonate and water. The organic layer was dried ($MgSO_4$), filtered, evaporated in vacuo and the residue purified by reverse phase HPLC. After evaporation in vacuo the oily residue was treated with ether to give a solid, filtered off and dried to yield the title compound as a white solid (60 mg).

MS (APCI−) 411 [M−H]− $^1$H NMR (DMSO-d6) δ 9.04 (1H, d), 8.19 (1H, s), 7.68 (1H, d), 7.65 (1H, d), 7.59 (2H, m), 7.32 (1H, d), 7.14 (1H, s), 4.87 (2H, dd), 4.21 (2H, dd), 2.27 (3H, s)

EXAMPLE 59

5-Chloro-3-(7-chloro-5,8-dihydro-4-quinolinyl)-2-(1-pyrrolidinylmethyl)-1H-indole-1-acetic acid 1-Bromo-2,5-pyrrolidinedione (165 mg) was added to a solution of the product from Example 27 (0.3 g) in DMF (3 ml), and the solution stirred for 10 min. Pyrrolidine (0.5 ml) was then added and the mixture stirred for a further 30 min. The solvents were evaporated in vacuo and the residue purified by reverse phase HPLC. After evaporation in vacuo the oily residue was treated with ether to give a solid which was filtered off and dried to yield the title compound as a white solid (70 mg).

MS (APCI+) 454 [M+H]+ $^1$H NMR DMSO-d6) δ 9.03 (1H, d), 8.18 (1H, s), 7.66 (1H, d), 7.57 (3H, m), 7.26 (1H, d), 7.09 (1H, s), 5.00 (2H, s), 3.97 (2H, dd), 2.46 (4H, m), 1.56 (4H, m)

EXAMPLE 60

5-Chloro-3-(7-chloro-4-quinolinyl)-2-[(methylthio)methyl]-1H-indole-1-acetic acid 1-Bromo-2,5-pyrrolidinedione (0.11 g) was added to a solution of the product from Example 27 step b) (0.2 g) in DMF (2 ml), and the solution stirred for 10 min. Sodium thiomethoxide (43 mg) was then added and the mixture stirred for a further 3 hours. The solvents were evaporated in vacuo and the residue purified by reverse phase HPLC. The residue was triturated with ether to give a solid, which was filtered and dried to yield the title compound as a white solid (40 mg).

MS (APCI+) 429 [M+H]+ $^1$H NMR (DMSO-d6) δ 9.02 (1H, d), 8.18 (1H, s), 7.67 (1H, d), 7.58 (3H, m), 7.24 (1H, d), 7.05 (1H, s), 5.18 (2H, s), 3.85 (2H, dd), 1.69 (3H, s)

EXAMPLE 61

5-Chloro-3-(7-chloro-4-quinolinyl)-2-[(methylsulfonyl)methyl]-1H-indole-1-acetic acid 1-Bromo-2,5-pyrrolidinedione (0.11 g) was added to a solution of the product from Example 27 step b) (0.2 g) in DMF (5 ml), and the solution stirred for 10 min. Sodium methanesulfinate (63 mg) was then added and the mixture stirred for a further 3 hours. The solvents were evaporated in vacuo and the residue purified by reverse phase HPLC. After evaporation in vacuo the oily residue was treated with ether to give a solid. Filtered off and dried to yield the title compound as a white solid (50 mg).

MS (APCI+) 461 [M+H]+ $^1$H NMR (DMSO-d6) δ 9.02 (1H, d), 8.18 (1H, s), 7.67 (1H, d), 7.61 (1H, d), 7.57 (2H, m), 7.27 (1H, d), 7.01 (1H, s), 5.18 (2H, s), 4.74 (2H, dd), 3.57, 2.91 (3H, s)

EXAMPLE 62

3-(7-Chloro-4-quinolinyl)-4-methoxy-2-methyl-1H-indole-1-acetic acid a) 4-(4-Methoxy-2-methyl-1H-indol-3-yl)-8-methyl-quinoline hydrochloride The sub-title compound was prepared by the method of Example 15 step a) using 4-methoxy-2-methylindole and 4,7-chloroquinoline.

MS: ESI (+ve): 324 [M−Cl]+ b) Ethyl 3-(7-chloro-74-quinolinyl)-4-methoxy-2-methyl-1H-indole-1-acetate

The sub-title compound was prepared by the method of Example 15 step b) using the product of step a).

MS: ESI (+ve): 409 [M+H]+ c) 3-(7-Chloro-4-quinolinyl)-4-methoxy-2-methyl-1H-indole-1-acetic acid

The title compound was prepared by the method of Example 15 step c) using the product of step b).

MS: ESI (+ve): 381 [M+H]+, 100%. $^1$H NMR (300MHz, DMSO-d6) δ 13.12 (1H, s), 8.93 (1H, d), 8.10 (1H, d), 7.62 (1H, d), 7.51 (1H, dd), 7.42 (1H, d), 7.16-7.07 (2H, m), 6.55 (1H, d), 5.08 (2H, s), 3.36 (3H, s), 2.13 (3H, s)

EXAMPLE 63

5-chloro-2-methyl-3-[8-(trifluoromethyl)-4-quinolinyl]-1H-indole-1-acetic acid a) 4-(5-chloro-2-methyl-3H-indol-3-yl)-8-(trifluoromethyl)quinoline The sub-title compound was prepared by the method of Example 10 step a) using 5-chloro-2-methylindole and 4-chloro-6-trifluoromethylquinoline.

MS: ESI (+ve): 435/37 [M+H]+ b) 5-chloro-2-methyl-3-[8-(trifluoromethyl)-4-quinolinyl]-1H-indole-1-acetic acid, ethyl ester The sub-title compound was prepared by the method of Example 10 step b) using the product of step a) to give an oil 0.5 g which was used in step c) without further purification.

c) 5-chloro-2-methyl-3-[8-(trifluoromethyl)-4-quinolinyl]-1H-indole-1-acetic acid The title compound was prepared by the method of Example 27 step b) using the product of step b).

MS: APCI (−ve): 419/21[M−H]− $^1$H NMR (DMSO-d6) δ 9.1 (1H, d), 8.24 (1H, d), 7.96 (1H, d), 7.69 (1H, t); 7.66-7.61 (2H, m), 7.2 (1H, d), 7.14 (1H, s) 5.16 (2H, dd), 2.28 (3H, s).

EXAMPLE 64

5-Cyano-2-methyl-3-(8-methyl-4-quinolinyl)-1H-indole-1-acetic acid a) 5-Cyano-2-methyl-1H-indole 5-Cyano-2-methyl-3-methylthio-1H-indole was prepared from 4-cyanoaniline by the method of example 48, part a) and used to prepare the subtitle compound by the method of example 48, part b).

$^1$H NMR (DMSO-d6) δ 11.53 (s, 1H), 7.91 (1H, s), 7.42 (1H, d), 7.33 (1H, d), 6.27 (1H, s), 2.41 (3H, s).

b) Methyl 5-Cyano-2-methyl-3-(8-methyl-4-quinolinyl)-1H-indole-1-acetate

A solution of the product from part a) (468 mg) and 4-chloro-8-methylquinoline (533 mg) in NMP (1 ml) and 4M hydrogen chloride in dioxane (1 ml) was stirred at 150° C. overnight and evaporated. The residue was taken up in ethyl acetate, washed with brine (3×), dried (MgSO$_4$) and evaporated. The residue was taken up in acetone (20 ml) treated with cesium carbonate (2.44 g) followed by methyl bromoacetate (0.64 ml), heated under reflux overnight and evaporated. The residue was taken up in ethyl acetate, washed with brine (3×), dried (MgSO$_4$) and evaporated. The residue was purified by silica chromatography using 20% acetone in isohexane as eluent to give the subtitle compound.

$^1$H NMR (CDCl$_3$) δ 9.04 (1H, d), 7.62-7.59 (2H, m), 7.53-7.48 (2H, m), 7.39-7.34 (3H, m), 4.97 (2H, s), 3.84 (3H, s), 2.91 (3H, s), 2.31 (3H, s)

c) 5-Cyano-2-methyl-3-(8-methyl-4-quinolinyl)-1H-indole-1-acetic acid

The product from step b) was taken up in THF (10 ml) treated with a solution of lithium hydroxide (252 mg) in water (10 ml) and stirred for 1 hour. The solution was concentrated to remove the THF and acidified with saturated aqueous potassium hydrogen sulphate. The solid was collected by filtration, washed with water, washed with a little cold propan-2-ol, washed with a little cold ether and dried to give the title compound as a yellow/orange solid (606 mg).

$^1$H NMR (DMSO-d6) δ 9.01 (1H, d), 7.79 (1H, d), 7.66 (1H, d), 7.58-7.41 (5H, m), 5.23 (2H, s), 2.81 (3H, s), 2.25 (3H, s) MS: ASI (−ve): 354 [M−1]

EXAMPLE 65

5-Cyano-2-methyl-3-[8-(trifluoromethyl)-4-quinolinyl]-1H-indole-1-acetic acid a) Methyl 5-Cyano-2-methyl-3-(8-trifluoromethyl-4-quinolinyl)-1H-indole-1-acetate The sub-title compound was prepared from the product of example 55, step a) and 4-chloro-8-trifluoromethylquinoline by the method of example 55, step b).

$^1$H NMR (CDCl$_3$) δ 9.17 (1H, d), 8.13 (1H, d), 7.91 (1H, d), 7.56-7.49 (4H, m), 7.38 (1H, d), 4.99 (2H, s), 3.85 (3H, s), 2.33 (3H, s)

b) 5-Cyano-2-methyl-3-[8-(trifluoromethyl)-4-quinolinyl]-1H-indole-1-acetic acid The title compound was prepared from the product from step a) by the method of example 55, step c).

$^1$HNMR (DMSO-d6) δ 13.32 (1H, s), 9.14 (1H, d), 8.24 (1H, d), 7.93 (1H, d), 7.81 (1H, d), 7.73-7.68 (3H, m), 7.58 (1H, dd), 5.27 (2H, s), 2.27 (3H, s) MS: APCI (−ve): 408 [M−1]

EXAMPLE 66

3-(7-Chloro-4-quinolinyl)-5-cyano-2-methyl-1H-indole-1-acetic acid a) Methyl 5-Cyano-2-methyl-3-(8-trifluoromethyl-4-quinolinyl)-1H-indole-1-acetate The sub-title compound was prepared from the product of example 55, step a) and 4,7-dichloroquinoline by the method of example 55, step b).

$^1$H NMR (CDCl$_3$) δ 9.03 (1H, d), 8.46 (1H, s), 7.72 (1H, d), 7.60 (2H, d), 7.55-7.52 (3H, m), 7.39 (1H, d), 4.99 (2H, s), 3.86 (3H, s), 2.35 (3H, s)

b) 5-Cyano-2-methyl-3-[8-(trifluoromethyl)-4-quinolinyl]-1H-indole-1-acetic acid The title compound was prepared from the product from step a) by the method of example 55, step c).

$^1$H NMR (DMSO-d6) δ 9.03 (1H, d), 8.19 (1H, d), 7.81 (1H, d), 7.68-7.56 (5H, m), 5.26 (2H, s), 2.27 (3H, s) MS: APCI (−ve): 374 [M−1]

EXAMPLE 67

3-(8-Chloro-4-quinolinyl)-5-cyano-2-methyl-1H-indole-1-acetic acid a) Methyl 3-(8-chloro-4-quinolinyl)-5-cyano-2-methyl-1H-indole-1-acetate The sub-title compound was prepared from the product of example 55, step a) and 4,8-dichloroquinoline by the method of example 55, step b).

$^1$H NMR (CDCl$_3$) δ 9.14 (1H, d), 7.89 (1H, d), 7.62 (1H, d), 7.57 (1H, s), 7.52-7.46 (2H, m), 7.43-7.35 (2H, m), 4.98 (2H, s), 3.85 (3H, s), 2.32 (3H, s)

b) 5-Cyano-2-methyl-3-[8-(trifluoromethyl)-4-quinolinyl]-1H-indole-1-acetic acid The title compound was prepared from the product from step a) by the method of example 55, step c).

$^1$H NMR (DMSO-d6) δ 9.11 (1H, d), 8.01 (1H, d), 7.81 (1H, d), 7.66-7.52 (5H, m), 5.26 (2H, s), 2.26 (3H, s) MS: APCI (−ve): 374 [M−1]

EXAMPLE 68

5-Cyano-2-methyl-3-(2-methyl-4-quinolinyl)-1H-indole-1-acetic acid a) Methyl 5-Cyano-2-methyl-3-(2-methyl-4-quinolinyl)-1H-indole-1-acetate The sub-title compound was prepared from the product of example 55, step a) and 4-chloro-2-methylquinoline by the method of example 55, step b).

$^1$H NMR (CDCl$_3$) δ 8.13 (1H, d), 7.74-7.69 (1H, m), 7.62-7.59 (2H, m), 7.49 (1H, dd), 7.44-7.39 (1H, m), 7.36 (1H, d), 7.29 (1H, s), 4.97 (2H, s), 3.84 (3H, s), 2.82 (3H, s), 2.32 (3H, s)

b) 5-Cyano-2-methyl-3-[8-(trifluoromethyl)-4-quinolinyl]-1H-indole-1-acetic acid The title compound was prepared from the product from step a) by the method of example 55, step c).

¹H NMR (DMSO-d6) δ 8.07 (1H, d), 7.82-7.79 (2H, m), 7.67-7.53 (5H, m), 5.26 (2H, s), 2.78 (3H, s), 2.26 (3H, s) MS: APCI (−ve): 354 [M−1]

EXAMPLE 69

3-(8-chloro-4-quinolinyl)-5-fluoro-2-methyl-1H-indole-1-acetic acid a) 8-chloro-4-(5-fluoro-2-methyl-1H-indol-3-yl)-quinoline
The sub-title compound was made by the method of example 31 step a) using 5-fluoro-2-methylindole and 4,8-dichloroquinoline.
b) 3-(8-chloro-4-quinolinyl)-5-fluoro-2-methyl-1H-indole-1-acetic acid
The title compound was made by the method of example 31 step b) using the product from step a).
MS: APCI (−ve): 367 [M—1] ¹H NMR (DMSO-d6) δ 9.06 (1H, d), 7.97 (1H, d), 7.73 (1H, d), 7.60-7.38 (3H, m), 6.95 (1H, m), 6.85 (1H, m), 4.66 (2H, s), 2.23 (3H, s)

EXAMPLE 70

5-fluoro-2-methyl-3-(7-methyl-4-quinolinyl)-1H-indole-1-acetic acid a) 4-(5-fluoro-2-methyl-1H-indol-3-yl)-7-methyl-quinoline
The subtitle compound was made by the method of example 31 step a) using 5-fluoro-2-methylindole and 4-chloro-7-methylquinoline.
b) 5-fluoro-2-methyl-3-(7-methyl-4-quinolinyl)-1H-indole-1-acetic acid
The title compound was made by the method of example 31 step b) using the product from step a).
MS: APCI (−ve):347 (M−1) ¹H NMR (DMSO-d6) δ 8.01 (1H, d), 7.76-7.61 (2H, m), 7.56-7.39 (2H, m), 7.37 (1H, s), 6.98 (1H, t), 6.85 (1H, m), 4.98 (2H, s), 2.71 (3H, s), 2.23 (3H, s)

EXAMPLE 71

2-methyl-5-(trifluoromethyl)-3-[8-(trifluoromethyl)-4-quinolinyl]-1H-indole-1-acetic acid a) 4-[2-methyl-5-(trifluoromethyl)-1H-indol-3-yl]-8-(trifluoromethyl)-quinoline
The subtitle compound was made by the method of example 31 step a) using 2-methyl-5-(trifluoromethyl)-indole and 4-chloro-8-(trifluoromethyl)-quinoline.
b) 2-methyl-5-(trifluoromethyl)-3-[8-(trifluoromethyl)-4-quinolinyl]-1H-indole-1-acetic acid
The title compound was made by the method of example 31 step b) using the product from step a).
MS: APCI (−ve): 451 (M−1) ¹H NMR (DMSO-d6) δ 9.13 (1H, d), 8.22 (1H, d), 7.97 (1H, d), 7.77-7.62 (3H, m), 7.46 (2H, d), 4.96 (2H, s), 2.29 (3H, s)

EXAMPLE 72

3-(8-fluoro-4-quinolinyl)-2-methyl-5-(trifluoromethyl)-1H-indole-1-acetic acid a) 8-fluoro-4-[2-methyl-5-(trifluoromethyl)-1H-indol-3-yl] quinoline
The sub-title compound was made by the method of example 31 step a) using 2-methyl-5-(trifluoromethyl)-indole and 4-chloro-8-fluoro-quinoline.
b) 3-(8-fluoro-4-quinolinyl)-2-methyl-5-(trifluoromethyl)-1H-indole-1-acetic acid
The title compound was made by the method of example 31 step b) using the product from step a).
MS: APCI (−ve): 401 [M−1] ¹H NMR DMSO-d6) δ 9.03 (1H, d), 7.74-7.38 (7H, m), 4.85 (2H, s), 2.28 (3H, s)

EXAMPLE 73

3-(8-chloro-4-quinolinyl)-2-methyl-5-(trifluoromethyl)-1H-indole-1-acetic acid a) 8-chloro-4-[2-methyl-5-(trifluoromethyl)-1H-indol-3-yl]-quinoline
The subtitle compound was made by the method of example 31 step a) using 2-methyl-5-(trifluoromethyl)-indole and 4,8-dichloroquinoline.
b) 3-(8-chloro-4-quinolinyl)-2-methyl-5-(trifluoromethyl)-1H-indole-1-acetic acid
The title compound was made by the method of example 31 step b) using the product from step a).
MS: APCI (−ve): 417 [M−1] ¹H NMR (DMSO-d6) 6.9.10 (1H, d), 7.98 (1H, d), 7.74-7.58 (3H, m), 7.56-7.38 (3H, m), 4.83 (2H, s), 2.29 (3H, s)

EXAMPLE 74

3-(8-chloro-4-quinolinyl)-2-methyl-5-(methylsulfonyl)-1H-indole-1-acetic acid a) 2-methyl-5-(methylsulfonyl)-1H-indole
2-methyl-5-(methylsulfonyl)-3-(methylthio)-1H-indole was prepared from 4-(methylsulfonyl)-aniline by the method of example 48, part a) and used to prepare the subtitle compound by the method of example 48, part b).
¹H NMR (DMSO-d6) δ11.50 (1H, s), 8.00 (1H, d), 7.63-7.35 (2H, m), 6.37 (1H, s), 3.13 (3H, s), 2.44 (3H, s)
b) 8-chloro-4-[2-methyl-5-(methylsulfonyl)-1H-indol-3-yl]-quinoline
The sub-title compound was made by the method of example 31 step a) using the product from step a) and 4,8-dichloroquinoline.
c) 3-(8-chloro-4-quinolinyl)-2-methyl-5-(methylsulfonyl)-1H-indole-1-acetic acid
The title compound was made by the method of example 31 step b) using the product from step b).
MS: APCI (−ve): 427 [M−1] ¹H NMR (DMSO-d6) δ 9.12 (1H, d), 8.00 (1H, d), 7.78-7.60 (5H, m), 7.54 (1H, d), 4.89 (2H, s), 3.12 (3H, s), 2.29 (3H, s)

EXAMPLE 75

2-methyl-3-(8-methyl-4-quinolinyl)-5-(methylsulfonyl)-1H-indole-1-acetic acid a) 8-methyl-4-[2-methyl-5-(methylsulfonyl)-1H-indol-3-yl]-quinoline
The sub-title compound was made by the method of example 31 step a) using 2-methyl-5-(methylsulfonyl)-1H-indole and 4-chloro-8-methylquinoline.
b) 2-methyl-3-(8-methyl-4-quinolinyl)-5-(methylsulfonyl)-1H-indole-1-acetic acid
The title compound was made by the method of example 31 step b) using the product from step a).

MS: APCI (−ve): 407 [M−1] $^1$H NMR (DMSO-d6) δ 9.03 (1H, d), 7.81-7.60 (4H, m), 7.55-7.35 (3H, m), 5.00 (2H, s), 3.10 (3H, s), 2.83 (3H, s), 2.29 (3H, s)

EXAMPLE 76

2-methyl-5-(methylsulfonyl)-3-[8-(trifluoromethyl)-4-quinolinyl]-1H-indole-1-acetic acid a) 4-[2-methyl-5-(methylsulfonyl)-1H-indol-3-yl]-8-(trifluoromethyl)-quinoline The sub-title compound was made by the method of example 31 step a) using 2-methyl-5-(methylsulfonyl)-1H-indole and 4-chloro-8-(trifluoromethyl)-quinoline.

b) 2-methyl-5-(methylsulfonyl)-3-[8-(trifluoromethyl)-4-quinolinyl]-1H-indole-1-acetic acid The title compound was made by the method of example 31 step b) using the product from step a).

MS: APCI (−ve): 461 (M−1) $^1$H NMR (DMSO-d6) δ 10.04 (1H, d), 9.13 (1H, d), 8.91 (1H, d), 8.62-8.51 (5H, m), 5.57 (2H, s), 4.01 (3H, s), 3.19 (3H, s)

EXAMPLE 77

3-(7-chloro-4-quinolinyl)-2-methyl-5-(methylsulfonyl)-1H-indole-1-acetic acid a) 7-chloro-4-[2-methyl-5-(methylsulfonyl)-1H-indol-3-yl]-quinoline The sub-title compound was made by the method of example 31 step a) using 2-methyl-5-(methylsulfonyl)-1H-indole and 4,7-dichloroquinoline.

b) 3-(7-chloro-4-quinolinyl)-2-methyl-5-(methylsulfonyl)-1H-indole-1-acetic acid The title compound was made by the method of example 31 step b) using the product from step a).

MS: APCI (−ve): 427 (M−1) $^1$H NMR (DMSO-d6) δ 9.04 (1H, d), 8.19 (1H, d), 7.80-7.56 (6H, m), 5.04 (2H, s), 3.12 (3H, s), 2.29 (3H, s)

EXAMPLE 78

5-chloro-2-methyl-3-[8-(methylsulfonyl)-4-quinolinyl]-1H-indole-1-acetic acid a) 4-(5-chloro-2-methyl-1H-indol-3-yl)-8-(methylsulfonyl)-quinoline The sub-title compound was prepared by the method of Example 40 step a, using 5-chloro-2-methyl-1H-indole and 8-methanesulphonyl-4-chloroquinoline.

MS: APCI (+ve): 371 [M+H]

b) 5-chloro-2-methyl-3-[8-(methylsulfonyl)-4-quinolinyl]-1H-indole-1-acetic acid, ethyl ester The sub-title compound was prepared by the method of Example 40 step b, using the product of step a.

MS: ESI (+ve): 457 [M+H]$^+$ c) 5-chloro-2-methyl-3-[8-(methylsulfonyl)-4-quinolinyl]-1H-indole-1-acetic acid The sub-title compound was prepared by the method of Example 40 step c, using the product of step b.

MS: ESI (−ve): 427 [M−H] $^1$HNMR (DMSO-d6) δ 9.15-7.42 (6H, M), 7.12-7.09 (2H, m), 4.54-4.45 (2H, m), 3.67 (3H, s), 2.23 (3H, s)

EXAMPLE 79

5-Fluoro-2-methyl-3[8-(methylsulfonyl)-4-quinolinyl]-1H-indole-1-acetic acid a) 4-(5-fluoro-2-methyl-1H-indol-3-yl)-8-(methylsulfonyl)-quinoline The sub-title compound was prepared by the method of Example 40 step a, using 5-fluoro-2-methyl-1H-indole and 8-methanesulphonyl-4-chloroquinoline.

MS: APCI (+ve): 355 [M+H]

b) 5-fluoro-2-methyl-3-[8-(methylsulfonyl)-4-quinolinyl]-1H-indole-1-acetic acid, ethyl ester The sub-title compound was prepared by the method of Example 40 step b, using the product of step a.

MS: ESI (+ve): 441 [M+H]$^+$ c) 5-fluoro-2-methyl-3-[8-(methylsulfonyl)-4-quinolinyl]-1H-indole-1-acetic acid The sub-title compound was prepared by the method of Example 40 step c, using the product of step b.

MS: ESI (−ve): 411 [M+H] $^1$H NMR (DMSO-d6) δ 9.13-7.39 (6H, M), 6.97-6.86 (2H, m), 4.53-4.44 (2H, m), 3.67 (3H, s), 2.24 (3H, s).

REFERENCES

1) Gassmann, Berge, T. J., Gilbert, D. P., Berkeley, W. C., *JACS*, 96, 5495-5508, (1974).

Pharmacological Data

Ligand Binding Assay

[$^3$H]PGD$_2$ was purchased from Perkin Elmer Life Sciences with a specific activity of 100-210 Ci/mmol. All other chemicals were of analytical grade.

HEK cells expressing rhCRTh2/Gα16 were routinely maintained in DMEM containing 10% Fetal Bovine Serum (HyClone), 1 mg/ml geneticin, 2 mM L-glutamine and 1% non-essential amino acids. For the preparation of membranes, the adherent transfected HEK cells were grown to confluence in two layer tissue culture factories (Fisher, catalogue number TKT-170-070E). Maximal levels of receptor expression were induced by addition of 500 mM sodium butyrate for the last 18 hours of culture. The adherent cells were washed once with phosphate buffered saline (PBS, 50 ml per cell factory) and detached by the addition of 50 ml per cell factory of ice-cold membrane homogenisation buffer [20 mM HEPES (pH 7.4), 0.1 mM dithiothreitol, 1 mM EDTA, 0.1 mM phenyl methyl sulphonyl fluoride and 100 μg/ml bacitracin]. Cells were pelleted by centrifugation at 220×g for 10 minutes at 4° C., re-suspended in half the original volume of fresh membrane homogenisation buffer and disrupted using a Polytron homogeniser for 2×20 second bursts keeping the tube in ice at all times. Unbroken cells were removed by centrifugation at 220×g for 10 minutes at 4° C. and the membrane fraction pelleted by centrifugation at 90000×g for 30 minutes at 4° C. The final pellet was re-suspended in 4 ml of membrane homogenisation buffer per cell factory used and the protein content determined. Membranes were stored at −80° C. in suitable aliquots.

All assays were performed in Corning clear bottomed, white 96-well NBS plates (Fisher). Prior to assay, the HEK cells membranes containing CRTh2 were coated onto SPA PVT WGA beads (Amersham). For coating membranes were incubated with beads at typically 25 μg membrane protein per mg beads at 4° C. with constant agitation overnight. (The optimum coating concentrations were determined for each batch of membranes) The beads were pelleted by centrifugation (800×g for 7 minutes at 4° C.), washed once with assay buffer (50 mM HEPES pH 7.4 containing 5 mM magnesium chloride) and finally re-suspended in assay buffer at a bead concentration of 10 mg/ml.

Each assay contained 20 µl of 6.25 nM [$^3$H]PGD$_2$, 20 µl membrane saturated SPA beads both in assay buffer and 10 µl of compound solution or 13,14-dihydro-15-keto prostaglandin D$_2$ (DK-PGD$_2$, for determination of non-specific binding, Cayman chemical company). Compounds and DK-PGD$_2$ were dissolved in DMSO and diluted in the same solvent to 100× the required final concentration. Assay buffer was added to give a final concentration of 10% DMSO (compounds were now at 10× the required final concentration) and this was the solution added to the assay plate. The assay plate was incubated at room temperature for 2 hours and counted on a Wallac Microbeta liquid scintillation counter (1 minute per well).

Compounds of formula (I) have an IC$_{50}$ value of less than (<) 10 µM. Specifically, example 14 has a pIC$_{50}$=7.7, example 36 has a pIC$_{50}$=8.15 and example 55 has a pIC$_{50}$=7.27.

The invention claimed is:

1. A compound of formula (I) or a pharmaceutically acceptable salt or solvate thereof:

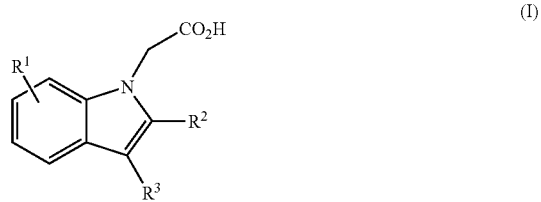

(I)

in which
R$^1$ is hydrogen, halogen, CN, nitro, SO$_2$R$^4$, OH, OR$^4$, SR$^4$, SOR$^4$, SO$_2$NR$^5$R$^6$, CONR$^5$R$^6$, NR$^5$R$^6$, NR$^9$SO$_2$R$^4$, NR$^9$CO$_2$R$^4$, NR$^9$COR$^4$, heteroaryl, aryl (optionally substituted by chlorine or fluorine), C$_2$-C$_6$ alkenyl, C$_2$-C$_6$ alkynyl or C$_1$-C$_6$alkyl, the latter three groups being optionally substituted by one or more substituents independently selected from halogen, OR$^8$ and NR$^5$R$^6$, S(O)$_x$R$^7$ where x is 0, 1 or 2;
R$^2$ is hydrogen, halogen, CN, SO$_2$R$^4$ or CONR$^5$R$^6$, CH$_2$OH, CH$_2$OR$^4$ or C$_1$-C$_7$alkyl, the latter group being optionally substituted by one or more substituents independently selected from halogen atoms, OR$^8$ and NR$^5$R$^6$, S(O)$_x$R$^7$ where x is 0, 1 or 2;
R$^3$ is quinoline, which is optionally substituted by one or more substituents independently selected from hydrogen, halogen, CN, nitro, OH, SO$_2$R$^4$, OR$^4$, SR$^4$, SOR$^4$, SO$_2$NR$^5$R$^6$, CONR$^5$R$^6$, NR$^5$R$^6$, NR$^9$SO$_2$R$^4$, NR$^9$CO$_2$R$^4$, NR$^9$CO$_2$H, NR$^9$COR$^4$, C$_2$-C$_6$ alkenyl, C$_2$-C$_6$ alkynyl, C$_1$-$_6$alkyl, the latter three groups being optionally substituted by one or more substituents independently selected from halogen atoms, OR$^8$ and NR$^5$R$^6$, S(O)$_x$R$^7$ where x=0, 1 or 2;
R$^4$ represents aryl, heteroaryl, or C$_1$-$_6$alkyl all of which may be optionally substituted by one or more substituents independently selected from halogen atoms, aryl, heteroaryl, OR$^{10}$ and NR$^{11}$R$^{12}$, S(O)$_x$R$^{13}$ (where x=0, 1 or 2), CONR$^{14}$R$^{15}$, NR$^{14}$COR$^{15}$, SO$_2$NR$^{14}$R$^{15}$, NR$^{14}$SO$_2$R$^{15}$;
R$^5$ and R$^6$ independently represent a hydrogen atom, a C$_1$-$_6$alkyl group, or an aryl, or a heteroaryl, the latter three of which may be optionally substituted by one or more substituents independently selected from halogen atoms, aryl, OR$^8$ and NR$^{14}$R$^{15}$, CONR$^{14}$R$^{15}$, NR$^{14}$COR$^{15}$, SO$_2$NR$^{14}$R$^{15}$, NR$^{14}$SO$_2$R$^{15}$; or
R$^5$ and R$^6$ together with the nitrogen atom to which they are attached can form a 3-8 membered saturated heterocylic ring optionally containing one or more atoms selected from O, S(O)$_x$ where x=0, 1 or 2, NR$^{16}$, and itself optionally substituted by C$_{1-3}$ alkyl;
R$^7$ and R$^{13}$ independently represent a C$_1$-C$_6$, alkyl, an aryl or a heteroaryl group all of which maybe optionally substituted by one or more halogen atoms;
R$^8$ represents a hydrogen atom, C(O)R$^9$, C$_1$-C$_6$ alkyl an aryl or a heteroaryl group, all of which may be optionally substituted by halogen atoms or an aryl group;
each of R$^9$ R$^{10}$, R$^{11}$, R$^{12}$, R$^{14}$, R$^{15}$, independently represents a hydrogen atom, C$_1$-C$_6$ alkyl, an aryl or a heteroaryl group, all of which may be optionally substituted by a halogen atom; and
R$^{16}$ is hydrogen, C$_{1-4}$ alkyl, —COC$_1$—C$_4$ alkyl, COYC$_1$—C$_4$alkyl where Y is O or NR$^7$.

2. A compound according to claim 1 in which R$^1$ is hydrogen or C$_{1-6}$alkyl optionally substituted by halogen, C$_{1-6}$alkoxy, alkylsulfone, cyano, NR$^9$SO$_2$R$^4$ or NR$^9$COR$^4$.

3. A compound according to claim 1 in which R$^2$ is hydrogen, C$_{1-6}$alkyl or C$_{1-6}$alkyl optionally substituted by OR$^8$.

4. A compound according to claim 3 in which R$^3$ is quinoline is attached to the indole at the 4 position.

5. A compound according to claim 1 in which the substituent(s) on R$^3$ is (are) hydrogen, methyl, trifluoromethyl, methoxy, fluoro, chloro, methylsulfone or cyano.

6. A compound according to claim 1 selected from:
3-(2-chloro-4-quinolinyl)-2,5-dimethyl-1H-indole-1-acetic acid;
3-(2-chloro-4-quinolinyl)-2-methyl-1H-indole-1-acetic acid;
3-(2-chloro-4-quinolinyl)-1H-indole-1-acetic acid;
2-methyl-3-(4-quinolinyl)-1H-indole-1-acetic acid;
3-(2-chloro-4-quinolinyl)-5-methoxy-2-methyl-1H-indole-1-acetic acid;
3-(2-chloro-4-quinolinyl)-2,6-dimethyl-1H-indole-1-acetic acid;
3-(2-chloro-4-quinolinyl)-2,4-dimethyl-1H-indole-1-acetic acid;
2,5-dimethyl-3-(7-methyl-4-quinolinyl)-1H-indole-1-acetic acid;
2,5-dimethyl-3-(8-methyl-4-quinolinyl)-1H-indole-1-acetic acid;
3-(6-fluoro-4-quinolinyl)-2,5-dimethyl-1H-indole-1-acetic acid;
3-(6-methoxy-4-quinolinyl)-2,5-dimethyl-1H-indole-1-acetic acid;
2,5-dimethyl-3-(4-quinolinyl)-1H-indole-1-acetic acid;
2,5-dimethyl-3-[8-(trifluoromethyl)-4-quinolinyl]-1H-indole-1-acetic acid;
3-(7-chloro-4-quinolinyl)-2,5-dimethyl-6-(methylsulfonyl)-1H-indole-1-acetic acid;
3-(8-fluoro-4-quinolinyl)-2,5-dimethyl-1H-indole-1-acetic acid;
3-(2,8-dimethyl-4-quinolinyl)-2,5-dimethyl-1H-indole-1-acetic acid;
2,5-dimethyl-3-[7-(trifluoromethyl)-4-quinolinyl]-1H-indole-1-acetic acid;
3-(8-bromo-2-methyl-4-quinolinyl)-2,5-dimethyl-1H-indole-1-acetic acid;
3-(8-methoxy-2-methyl-4-quinolinyl)-2,5-dimethyl-1H-indole-1-acetic acid;

3-(6,8-dimethyl-4-quinolinyl)-2,5-dimethyl-1H-indole-1-acetic acid;
3-(8-chloro-4-quinolinyl)-2,5-dimethyl-1H-indole-1-acetic acid;
3-(7-chloro-4-quinolinyl)-2-methyl-5-nitro-1H-indole-1-acetic acid;
5-chloro-3-(7-chloro-4-quinolinyl)-2-methyl-1H-indole-1-acetic acid;
5-chloro-2-methyl-3-(8-methyl-4-quinolinyl)-1H-indole-1-acetic acid;
5-chloro-3-(6-methoxy-2-methyl-4-quinolinyl)-2-methyl-1H-indole-1-acetic acid;
5-methoxy-2-methyl-3-(8-methyl-4-quinolinyl)-1H-indole-1-acetic acid, sodium salt;
3-(7-chloro-4-quinolinyl)-5-fluoro-2-methyl-1H-indole-1-acetic acid;
5-fluoro-2-methyl-3-[8-(trifluoromethyl)-4-quinolinyl]-1H-indole-1-acetic acid;
5-fluoro-2-methyl-3-(8-methyl-4-quinolinyl)-1H-indole-1-acetic acid;
2-methyl-3-(8-methyl-4-quinolinyl)-5-(trifluoromethyl)-1H-indole-1-acetic acid;
3-(8-nitroquinolin-4-yl)-2,5-dimethyl-1H-indole-1-acetic acid;
3-(8-cyano-4-quinolinyl)-2,5-dimethyl-1H-indole-1-acetic acid;
2,5-dimethyl-3-[8-(methylsulfonyl)-4-quinolinyl]-1H-indole-1-acetic acid;
3-[8-(difluoromethoxy)-4-quinolinyl]-2,5-dimethyl-1H-indole-1-acetic acid;
5-amino-3-(7-chloro-4-quinolinyl)-2-methyl-1H-indole-1-acetic acid;
3-(7-chloro-4-quinolinyl)-2-methyl-5-[(methylsulfonyl)amino]-1H-indole-1-acetic acid;
5-(acetylamino)-3-(7-chloro-4-quinolinyl)-2-methyl-1H-indole-1-acetic acid;
3-(7-chloro-4-quinolin-4-yl )-5-fluoro-2,4-dimethyl-1H-indol-1-yl] acetic acid;
5-chloro-2-methyl-3-(8-quinolinyl)-1H-indole-1-acetic acid;
5-chloro-3-(7-chloro-4-quinolinyl)-2-(hydroxymethyl)-1H-indole-1-acetic acid;
5-chloro-3-(7-chloro-4-quinolinyl)-2-(methoxymethyl)-1H-indole-1-acetic acid;
2-[(acetyloxy)methyl]-5-chloro-3-(7-chloro-4-quinolinyl)-1H-indole-1-acetic acid;
5-chloro-3-(7-chloro-4-quinolinyl)-2-[(methylamino)methyl]-1H-indole-1-acetic acid;
5-chloro-3-(7-chloro-4-quinolinyl)-2-[(methylthio)methyl]-1H-indole-1-acetic acid;
5-chloro-3-(7-chloro-4-quinolinyl)-2-[(methylsulfonyl)methyl]-1H-indole-1-acetic acid;
3-(7-chloro-4-quinolinyl)-4-methoxy-2-methyl-1H-indole-1-acetic acid;
5-chloro-2-methyl-3-[8-(trifluoromethyl)-4-quinolinyl]-1H-indole-1-acetic acid;
5-cyano-2-methyl-3-(8-methyl-4-quinolinyl)-1H-indole-1-acetic acid;
5-cyano-2-methyl-3-[8-(trifluoromethyl)-4-quinolinyl]-1H-indole-1-acetic acid;
3-(7-chloro-4-quinolinyl)-5-cyano-2-methyl-1H-indole-1-acetic acid;
3-(8-chloro-4-quinolinyl)-5-cyano-2-methyl-1H-indole-1-acetic acid;
5-cyano-2-methyl-3-(2-methyl-4-quinolinyl)-1H-indole-1-acetic acid;
3 -(8-chloro-4-quinolinyl)-5-fluoro-2-methyl-1H-indole-1-acetic acid;
5-fluoro-2-methyl-3-(7-methyl-4-quinolinyl)-1H-indole-1-acetic acid;
2-methyl-5-(trifluoromethyl)-3-[8-(trifluoromethyl)-4-quinolinyl]-1H-indole-1-acetic acid;
3-(8-fluoro-4-quinolinyl)-2-methyl-5-(trifluoromethyl)-1H-indole-1-acetic acid;
3-(8-chloro-4-quinolinyl)-2-methyl-5-(trifluoromethyl)-1H-indole-1-acetic acid;
3-(8-chloro-4-quinolinyl)-2-methyl-5-(methylsulfonyl)-1H-indole-1-acetic acid;
2-methyl-3-(8-methyl-4-quinolinyl)-5-(methylsulfonyl)-1H-indole-1-acetic acid;
2-methyl-5-(methylsulfonyl)-3-[8-(trifluoromethyl)-4-quinolinyl]-1H-indole-1-acetic acid;
3-(7-chloro-4-quinolinyl)-2-methyl-5-(methylsulfonyl)-1H-indole-1-acetic acid;
5-chloro-2-methyl-3-[8-(methylsulfonyl)-4-quinolinyl]-1H-indole-1-acetic acid;
5-fluoro-2-methyl-3-[8-(methylsulfonyl)-4-quinolinyl]-1H-indole-1-acetic acid;
and pharmaceutically acceptable salts thereof.

7. A method of treating asthma, which comprises administering to a patient a therapeutically effective amount of a compound of formula (I), or a pharmaceutically acceptable salt thereof as defined in claim 1.

8. A method of treating rhinitis, which comprises administering to a patient a therapeutically effective amount of a compound of formula (I), or a pharamaceutically acceptable salt therof as defined in claim 1.

9. A process for the preparation of a compound of formula (I) which comprises reaction of a compound of formula (II):

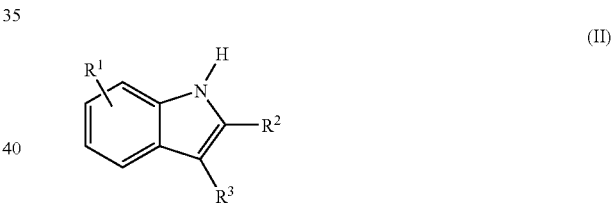

in which $R^1$, $R^2$ and $R^3$ are as defined in formula (I) or are protected derivatives thereof, with a compound of formula (III):

where $R^{17}$ is an ester forming group and L is a leaving group in the presence of a base, and optionally thereafter in any order:
  removing any protecting group
  hydrolysing the ester group $R^{17}$ to the corresponding acid
  forming a pharmaceutically acceptable salt.

10. A method of inhibiting the the CRTh2 receptor, the method comprising administering to a subject an effective amount of a compound of formula (I) or a pharmaceutically acceptable salt thereof as defined in claim 1.

11. The method according to claim 10 in which $R^1$ is hydrogen or $C_{1-6}$alkyl optionally substituted by halogen, $C_{1-6}$alkoxy, alkylsulfone, cyano, $NR^9SO_2R^4$ or $NR^9COR^4$.

12. The method according to claim 10 in which $R^2$ is hydrogen, $C_{1-6}$alkyl or $C_{1-6}$alkyl optionally substituted by $OR^8$.

* * * * *

UNITED STATES PATENT AND TRADEMARK OFFICE
CERTIFICATE OF CORRECTION

PATENT NO.       : 7,754,735 B2
APPLICATION NO.  : 10/516165
DATED            : July 13, 2010
INVENTOR(S)      : Timothy Birkinshaw et al.

It is certified that error appears in the above-identified patent and that said Letters Patent is hereby corrected as shown below:

Column 46, line 5, "heterocylic" should read -- heterocyclic --.

Column 46, line 15, "$R^9 R^{10}$," should read -- $R^9$, $R^{10}$, --.

Column 48, line 30, "pharamaceutically" should read -- pharmaceutically --.

Column 48, line 31, "therof" should read -- thereof --.

Column 48, line 55, delete the first occurrence of "the".

Signed and Sealed this

Sixteenth Day of November, 2010

David J. Kappos
*Director of the United States Patent and Trademark Office*